(12) United States Patent
Ross et al.

(10) Patent No.: US 8,892,171 B2
(45) Date of Patent: *Nov. 18, 2014

(54) SYSTEM AND METHOD FOR USER PROFILING FROM GATHERING USER DATA THROUGH INTERACTION WITH A WIRELESS COMMUNICATION DEVICE

(75) Inventors: David J. Ross, San Diego, CA (US); Eric C. Rosen, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 263 days.

This patent is subject to a terminal disclaimer.

(21) Appl. No.: 13/427,631

(22) Filed: Mar. 22, 2012

(65) Prior Publication Data

US 2013/0072169 A1    Mar. 21, 2013

Related U.S. Application Data

(63) Continuation-in-part of application No. 12/141,302, filed on Jun. 18, 2008.

(60) Provisional application No. 60/945,101, filed on Jun. 20, 2007.

(51) Int. Cl.
*H04M 19/04* (2006.01)
*H04W 4/00* (2009.01)
(Continued)

(52) U.S. Cl.
CPC .............. *H04W 4/00* (2013.01); *A61B 5/165* (2013.01); *A61B 5/6898* (2013.01);
(Continued)

(58) Field of Classification Search
CPC ............ A61B 5/02055; A61B 5/1112; A61B 5/14532; A61B 5/165; A61B 5/4803; A61B 5/6898; G06F 19/322; G06F 19/3406; G06F 19/3418; G06F 19/345; G06Q 30/02; H04L 67/306; H04M 1/7253; H04M 1/72561
USPC .......... 455/418, 414.1, 415, 456.1, 567, 557, 455/556.1, 521, 41.1, 41.2, 404.1, 412.1, 9; 340/870.01, 539.12; 705/14.66, 1; 709/217, 203, 204; 707/104.1; 370/395.4, 432

See application file for complete search history.

(56) References Cited

U.S. PATENT DOCUMENTS 5,490,275 A    2/1996   Sandvos et al.
6,298,047 B1  10/2001   Steffes et al.
(Continued)

FOREIGN PATENT DOCUMENTS

JP    10136444 A    5/1998
JP    2002142021 A  5/2002
(Continued)

OTHER PUBLICATIONS

European Search Report—EP10155057—Search Authority—Munich—Apr. 12, 2010.

(Continued)

*Primary Examiner* — Tan Trinh
(74) *Attorney, Agent, or Firm* — Michael F. Taveira

(57) ABSTRACT

A system, method, and wireless communication device that profiles a user thereof, or a user at a second wireless communication device in communication therewith. The wireless communication device gathers user data for a user thereof, or from a user at a second wireless communication device, and either directly generates, or has generated elsewhere, a user profile, such as a personality or psychological profile, or medical diagnosis of the user, and can display the user profile to the user and/or alter the wireless communication device functionality based upon the user profile. The gathered user data can be from a user interaction with the wireless communication device, from information available to the wireless communication device, or a combination thereof.

135 Claims, 14 Drawing Sheets

(51) Int. Cl.
- *A61B 5/16* (2006.01)
- *A61B 5/00* (2006.01)
- *G06F 19/00* (2011.01)
- *H04M 1/725* (2006.01)
- *G06Q 30/02* (2012.01)
- *H04N 21/258* (2011.01)
- *H04L 29/08* (2006.01)
- *A61B 5/0205* (2006.01)
- *A61B 5/11* (2006.01)
- *A61B 5/145* (2006.01)

(52) U.S. Cl.
CPC .......... *G06F 19/322* (2013.01); *G06F 19/3406* (2013.01); *G06F 19/3418* (2013.01); *G06F 19/345* (2013.01); *H04M 1/7253* (2013.01); *H04M 1/72563* (2013.01); *G06Q 30/02* (2013.01); *H04N 21/25891* (2013.01); *H04L 67/306* (2013.01); *A61B 5/02055* (2013.01); *A61B 5/1112* (2013.01); *A61B 5/14532* (2013.01); *A61B 5/4803* (2013.01); *H04M 1/72561* (2013.01); *H04M 1/72566* (2013.01); *H04M 1/72572* (2013.01); *H04M 2250/12* (2013.01)
USPC .................... 455/567; 455/556.1; 455/432.3; 715/745; 725/14; 705/14.1; 705/14.25; 705/26; 705/80

(56) References Cited

U.S. PATENT DOCUMENTS

| | | | |
|---|---|---|---|
| 6,661,437 B1* | 12/2003 | Miller et al. | 715/810 |
| 6,754,470 B2 | 6/2004 | Hendrickson et al. | |
| 7,212,990 B1 | 5/2007 | Greden et | |
| 7,920,702 B2* | 4/2011 | Shen-Orr et al. | 380/202 |
| 8,396,890 B2* | 3/2013 | Lim | 707/781 |
| 2002/0049770 A1 | 4/2002 | Mayadas | |
| 2002/0055872 A1 | 5/2002 | LaBrie et al. | |
| 2003/0125927 A1* | 7/2003 | Seme | 704/3 |
| 2003/0195934 A1 | 10/2003 | Peterson et al. | |
| 2004/0014423 A1 | 1/2004 | Croome et al. | |
| 2004/0014457 A1* | 1/2004 | Stevens | 455/414.1 |
| 2004/0168121 A1 | 8/2004 | Matz | |
| 2004/0177138 A1 | 9/2004 | Salle et al. | |
| 2004/0199923 A1 | 10/2004 | Russek | |
| 2004/0204048 A1* | 10/2004 | Lamensdorf | 455/556.1 |
| 2004/0243472 A1 | 12/2004 | Vadjinia | |
| 2005/0021666 A1* | 1/2005 | Dinnage et al. | 709/217 |
| 2005/0054381 A1* | 3/2005 | Lee et al. | 455/557 |
| 2005/0160458 A1 | 7/2005 | Baumgartner | |
| 2006/0183980 A1 | 8/2006 | Yang | |
| 2006/0217111 A1 | 9/2006 | Marolia et al. | |
| 2007/0061023 A1 | 3/2007 | Hoffberg et al. | |
| 2007/0073799 A1 | 3/2007 | Adjali et al. | |
| 2007/0117557 A1* | 5/2007 | Adjali et al. | 455/418 |
| 2007/0123222 A1 | 5/2007 | Cox et al. | |
| 2007/0143348 A1* | 6/2007 | Rosenberg | 707/104.1 |
| 2007/0155402 A1 | 7/2007 | Van Erlach | |
| 2007/0208602 A1* | 9/2007 | Nocera et al. | 705/8 |
| 2008/0027992 A1 | 1/2008 | Vadavia et al. | |
| 2008/0086318 A1 | 4/2008 | Gilley et al. | |
| 2008/0218376 A1* | 9/2008 | Dicks et al. | 340/870.01 |
| 2008/0255870 A1* | 10/2008 | Butler | 705/1 |
| 2008/0318563 A1 | 12/2008 | Ross et al. | |
| 2009/0006180 A1 | 1/2009 | Hameen-Anttila | |
| 2009/0043907 A1* | 2/2009 | Peterson et al. | 709/231 |
| 2009/0106664 A1 | 4/2009 | Corrao et al. | |
| 2009/0113319 A1 | 4/2009 | Dawson et al. | |
| 2009/0125510 A1 | 5/2009 | Graham et al. | |
| 2009/0157714 A1 | 6/2009 | Stanton et al. | |
| 2009/0249460 A1* | 10/2009 | Fitzgerald et al. | 726/7 |
| 2010/0069040 A1 | 3/2010 | Nath et al. | |
| 2010/0131584 A1 | 5/2010 | Johnson | |
| 2010/0144328 A1 | 6/2010 | Keating et al. | |
| 2011/0125063 A1 | 5/2011 | Shalon et al. | |
| 2011/0256852 A1* | 10/2011 | Stevens | 455/414.1 |
| 2011/0282750 A1* | 11/2011 | Rosen | 705/14.66 |
| 2011/0313776 A1* | 12/2011 | Alfred et al. | 704/275 |
| 2012/0054680 A1 | 3/2012 | Moonka et al. | |
| 2012/0149360 A1 | 6/2012 | Ross et al. | |
| 2012/0149993 A1 | 6/2012 | Ross et al. | |
| 2012/0157075 A1 | 6/2012 | Ross et al. | |
| 2012/0329475 A1* | 12/2012 | Ribaudo et al. | 455/456.1 |
| 2013/0253929 A1 | 9/2013 | WEIDER; Chris et al. | |

FOREIGN PATENT DOCUMENTS

| | | |
|---|---|---|
| JP | 2002290508 A | 10/2002 |
| JP | 2006074477 A | 3/2006 |
| WO | WO2007044328 A2 | 4/2007 |

OTHER PUBLICATIONS

International Preliminary Report on Patentability, PCT/US2008/067773, International Preliminary Examining Authority, European Patent Office, Sep. 3, 2009.
International Search Report—PCT/US08/067773, International Search Authority—European Patent Office—Jan. 29, 2009.
Partial International Search Report—PCT/US08067773, International Search Authority—European Patent Office—Sep. 2, 2008.
Written Opinion—PCT/US08/067773, International Search Authority—European Patent Office—Jan. 29, 2009.
International Search Report and Written Opinion—PCT/US2013/033495—ISA/EPO—May 16, 2013.
Partial European Search Report—EP10155057—Search Authority—The Munich—Apr. 12, 2010.

* cited by examiner

MYERS-BRIGGS — POSSIBLE UI CONFIGURATIONS

| | IS | ES | EN | IN |
|---|---|---|---|---|
| FP | Reserved I/F  search<br>Hidden Personal details<br>1:1<br>Splash Alert<br>Casual Mixed Layout<br>w/p<br>Colours & Images | Noise / Colour  search<br>Webcam<br>1:many<br>Splash Alert<br>Casual Mixed Layout<br>Colours & Images | Noise / Colour  help<br>Webcam<br>1:many<br>Splash Alert<br>Casual Mixed Layout  w/p<br>Colours & Images | Reserved I/F  help<br>Hidden Personal details<br>1:1<br>Splash Alert<br>Casual Mixed Layout<br>w/p<br>Colours & Images |
| FJ | Reserved I/F  search<br>Hidden Personal details<br>1:1<br>Ticker Tape Alert<br>Fixed Layout - separate<br>w&p<br>Colours & Images | Noise / Colour  search<br>Webcam<br>1:many<br>Ticker Tape Alert<br>Fixed Layout - separate<br>w&p<br>Colours & Images | Noise / Colour  help<br>Webcam<br>1:many<br>Ticker Tape Alert<br>Fixed Layout - separate<br>w&p<br>Colours & Images | Reserved I/F  help<br>Hidden Personal details<br>1:1<br>Ticker Tape Alert<br>Fixed Layout - separate<br>w&p<br>Colours & Images |
| TJ | Reserved I/F  search<br>Hidden Personal details<br>1:1<br>Ticker Tape Alert<br>Fixed Layout - separate<br>w&p<br>Words & Graphs | Noise / Colour  search<br>Webcam<br>1:many<br>Ticker Tape Alert<br>Fixed Layout - separate<br>w&p<br>Words & Graphs | Noise / Colour  help<br>Webcam<br>1:many<br>Ticker Tape Alert<br>Fixed Layout - separate<br>w&p<br>Words & Graphs | Reserved I/F  help<br>Hidden Personal details<br>1:1<br>Ticker Tape Alert<br>Fixed Layout - separate<br>w&p<br>Words & Graphs |
| TP | Reserved I/F  search<br>Hidden Personal details<br>1:1<br>Splash Alert<br>Casual Mixed Layout<br>w/p<br>Words & Graphs | Noise / Colour  search<br>Webcam<br>1:many<br>Splash Alert<br>Casual Mixed Layout<br>w/p<br>Words & Graphs | Noise / Colour  help<br>Webcam<br>1:many<br>Splash Alert<br>Casual Mixed Layout<br>Words & Graphs | Reserved I/F  help<br>Hidden Personal details<br>1:1<br>Splash Alert<br>Casual Mixed Layout<br>w/p<br>Words & Graphs |

FIG. 5

SYSTEM AND METHOD FOR USER PROFILING FROM GATHERING USER DATA THROUGH INTERACTION WITH A WIRELESS COMMUNICATION DEVICE

CROSS-REFERENCE TO RELATED APPLICATIONS

This application is a continuation-in-part of U.S. patent application Ser. No. 12/141,302 entitled "System And Method For User Profiling From Gathering User Data Through Interaction With A Wireless Communication Device" filed on Jun. 18, 2008 which claims the benefit of U.S. Provisional Patent Application Ser. No. 60/945,101, filed on Jun. 20, 2007, both of which are assigned to the assignee hereof are hereby incorporated herein by reference. This application is also related to U.S. patent application Ser. No. 13/398,005 entitled "System And Method For User Profiling From Gathering User Data Through Interaction With A Wireless Communication Device," filed on Feb. 16, 2012, U.S. patent application Ser. No. 13/398,057 entitled "System And Method For User Profiling From Gathering User Data Through Interaction With A Wireless Communication Device," filed on Feb. 16, 2012, U.S. patent application Ser. No. 13/398,179 entitled "System And Method For User Profiling From Gathering User Data Through Interaction With A Wireless Communication Device," filed on Feb. 16, 2012, and U.S. patent application Ser. No. 13/427,631 entitled "System And Method For User Profiling From Gathering User Data Through Interaction With A Wireless Communication Device," filed on Mar. 22, 2012, each of which claims the benefit of U.S. Provisional Patent Application Ser. No. 60/945,101, filed on Jun. 20, 2007.

BACKGROUND OF THE INVENTION

The invention relates to wireless communication devices that communicate across a wireless communication network. More particularly, the invention relates to a system and method for generating profiles for users of wireless communication devices based upon user interaction with the device.

Existent computing devices, to include wireless communication devices such as mobile phones, personal digital assistants (PDAs), interactive pagers, and other wireless computer platforms can alter their interactive functionality with the user. Typically, the user configures the functional parameters of the device, such as the user interface (UI), navigation choices such as screen presentation, and other items such as ring tones and automatic turn-off. Most of these functions are not adjusted automatically by the device, but are set in default parameters by the vendor until specifically adjusted by the user. Mobile computing devices also typically have limited resources such as bandwidth, processing capability, and power such that it is always preferably to limit device activity to conserve the device resources.

There are some computer devices that attempt to learn the preferences of the user of the device based upon user interaction with the device. For example, a computer device will often implement a "most recently used" algorithm with device functionality, thereby assuming that the most recently used item or function of the user of the device is the one most likely to be next desired by the user. Computer devices typically use only rudimentary algorithms that try to predict user desire based upon simple patterns of usage of the device because a more complex algorithm will require too much of the mobile device resources to implement. Consequently, without user modification, the computer device will not automatically significantly alter the device functionality for the user.

It is therefore desirous to have an ability to adequately profile the user of a wireless communication device and selectively modify wireless communication device functionality, based upon the profile of the specific user, and it is to such a system and method to provide this ability that this invention is primarily directed.

SUMMARY OF THE INVENTION

Briefly described, the present invention includes a system, method, and wireless communication device that profiles a user thereof, or a user at a second wireless communication device in communication therewith. The wireless communication device gathers user data for a user thereof, or from a user at a second wireless communication device, and either directly generates, or has generated elsewhere, a user profile, such as a psychological profile or medical diagnosis of the user, and can display the user profile to the user and/or alter the wireless communication device functionality based upon the user profile. The gathered user data can be from physical user interaction with the wireless communication device, or from data other equipment resident at the wireless communication device, such as a camera and medical diagnostic devices.

In one embodiment, the wireless communication device collects data about the specific device user, and creates a particular psychological or personality profile for a user, and maps those scores either directly or indirectly into UI configuration, responses and behavior. The wireless device can also reconfigure itself for multiple users of the same device where those multiple users may have different personalities. When these wireless communication devices are then in communication with other user devices, the respective profile data can be used to aid the user communications with each other.

In one embodiment, the system for altering wireless communication device functionality for wireless communication devices on a wireless communication network, such alteration based upon the user profile of the user of the wireless communication device, includes at least one wireless communication device configured to gather user data from physical user interaction with the wireless communication device. The wireless communication device has a functionality for user interaction, and the device can selectively transmit the gathered user data across the wireless communication network. At least one computer device receives the transmitted gathered user data and creates user profile data based upon the received gathered user data, and then transmits the user profile data back to the at least one wireless communication device. The wireless communication device can alter the wireless communication device functionality based upon the received user profile data.

In one embodiment, the method of profiling a user of a wireless communication device and altering the wireless communication device functionality based upon the user profile includes gathering user data from physical user interaction with the wireless communication device, the wireless communication device having a functionality for user interaction, and creating a user profile based upon the gathered user data. Then the device can alter the wireless communication device functionality based upon the gathered user data.

In one embodiment, the wireless communication device has a wireless communication device functionality based upon a user profile and gathers user data from physical user interaction, then creates a user profile based upon the gathered user data. However, the wireless communication device can selectively alter functionality based upon the gathered user data, but does not have to do so. The wireless device can also be equipped to gather medical data of the user and make a medical diagnosis as a user profile.

The various embodiments may include methods of altering a functionality of a wireless communication device by gathering data regarding a user of a first wireless communication device, creating a user profile based upon the gathered user data, transmitting the user profile to a second wireless communication device, and altering the functionality of the second wireless communication device based upon the user profile. In an embodiment, creating a user profile based upon the gathered user data may include interpreting data obtained from a calendar application of the first wireless communication device. In a further embodiment, interpreting data obtained from a calendar application of the first wireless communication device may include interpreting a user schedule. In a further embodiment, creating a user profile based upon the gathered user data may include interpreting types of software applications used by a user of the first wireless communication device.

In a further embodiment, creating a user profile based upon the gathered user data may include interpreting contents of communications on the first wireless communication device. In a further embodiment, interpreting contents of communications on the first wireless communication device may include interpreting content in an email message sent by a user of the first wireless communication device. In a further embodiment, creating a user profile based upon the gathered user data may include interpreting data obtained from a social media application of the first wireless communication device. In a further embodiment, creating a user profile based upon the gathered user data may include interpreting financial information relating to a user obtained from the first wireless communication device.

In a further embodiment, creating a user profile based upon the gathered user data may include interpreting data obtained from a web browser of the first wireless communication device. In a further embodiment, interpreting data obtained from a web browser of the first wireless communication device may include interpreting a history of Internet searches performed by the user using the web browser. In a further embodiment, interpreting data obtained from a web browser of the first wireless communication device may include interpreting types of websites accessed by the user using the web browser. In a further embodiment, interpreting data obtained from a web browser of the first wireless communication device may include interpreting content loaded from websites accessed by the user using the web browser.

In a further embodiment, creating a user profile based upon the gathered user data may include interpreting location information obtained from the first wireless communication device. In a further embodiment, interpreting location information obtained from the first wireless communication device may include interpreting information regarding movements of the first wireless communication device. In a further embodiment, creating a user profile based upon the gathered user data may include interpreting data obtained from a global positioning system receiver of first wireless communication device.

In a further embodiment, creating a user profile based upon the gathered user data may include interpreting data obtained from a media player operating on the first wireless communication device. In a further embodiment, creating a user profile based upon the gathered user data may include interpreting data obtained from a personal monitoring device. In a further embodiment, interpreting data obtained from a personal monitoring device may include interpreting data obtained from a heart rate monitor. In a further embodiment, interpreting data obtained from a personal monitoring device may include interpreting data obtained from a blood glucose meter. In a further embodiment, interpreting data obtained from a personal monitoring device may include interpreting data obtained from a breathalyzer.

In a further embodiment, creating a user profile based upon the gathered user data may include interpreting information regarding the user received from an external device in communication with the first wireless communication device. In a further embodiment, interpreting information regarding the user received from an external device in communication with the first wireless communication device may include interpreting information received from an external user monitoring device selected from the group of a medical monitoring device, and an exercise device. In a further embodiment, creating a user profile based upon the gathered user data may include interpreting information collected regarding the user of the first wireless communication device from an external database.

In a further embodiment creating a user profile based upon the gathered user data may include interpreting contents of a video recorded by the video camera of the first wireless communication device. In a further embodiment, creating a user profile may include performing a psychological evaluation based upon the gathered user data. In a further embodiment, creating a user profile may include making a medical diagnosis based upon the gathered user data. In a further embodiment, altering the functionality of the second wireless communication device may include altering a graphical user interface (GUI) of the second wireless communication device.

Further embodiments include a computing device having a processor configured with processor-executable instructions to perform various operations corresponding to the methods discussed above.

Further embodiments include a computing device that includes various means for performing operations corresponding to the method operations discussed above.

Further embodiments include a non-transitory processor-readable storage medium having stored thereon processor-executable instructions configured to cause a processor to perform various operations corresponding to the methods discussed above.

Further embodiments include a system that may include a first wireless communication device having a transmitter for transmitting wireless signals, a memory, and a processor coupled to the transmitter and the memory of the first wireless communication device, and a second wireless communication device having a receiver configured to receive signals transmitted by the transmitter, a memory, and a processor coupled to the receiver and memory of the second wireless communication device. Each of the first and second wireless communications devices may be configured with processor-executable instructions to perform various operations corresponding to the methods discussed above.

Other advantages and features of the present invention will become apparent after review of the hereinafter set forth Brief Description of the Drawings, Detailed Description of the Invention, and the Claims.

BRIEF DESCRIPTION OF THE DRAWINGS

FIG. 5 is a chart illustrating one embodiment of user interface (UI) configurations for a wireless communication device based upon a generated user profile being a personality type.

DETAIL DESCRIPTION OF THE INVENTION

In this description, the terms "communication device," "wireless device," "wireless communications device," "PTT communication device," "handheld device," "mobile device," and "handset" are used interchangeably. The terms "call" and "communication" are also used interchangeably. The term "application" as used herein is intended to encompass executable and non-executable software files, raw data, aggregated data, patches, and other code segments. The term "exemplary" means that the disclosed element or embodiment is only an example, and does not indicate any preference of user. Further, like numerals refer to like elements throughout the several views, and the articles "a" and "the" includes plural references, unless otherwise specified in the description.

Figure 1:
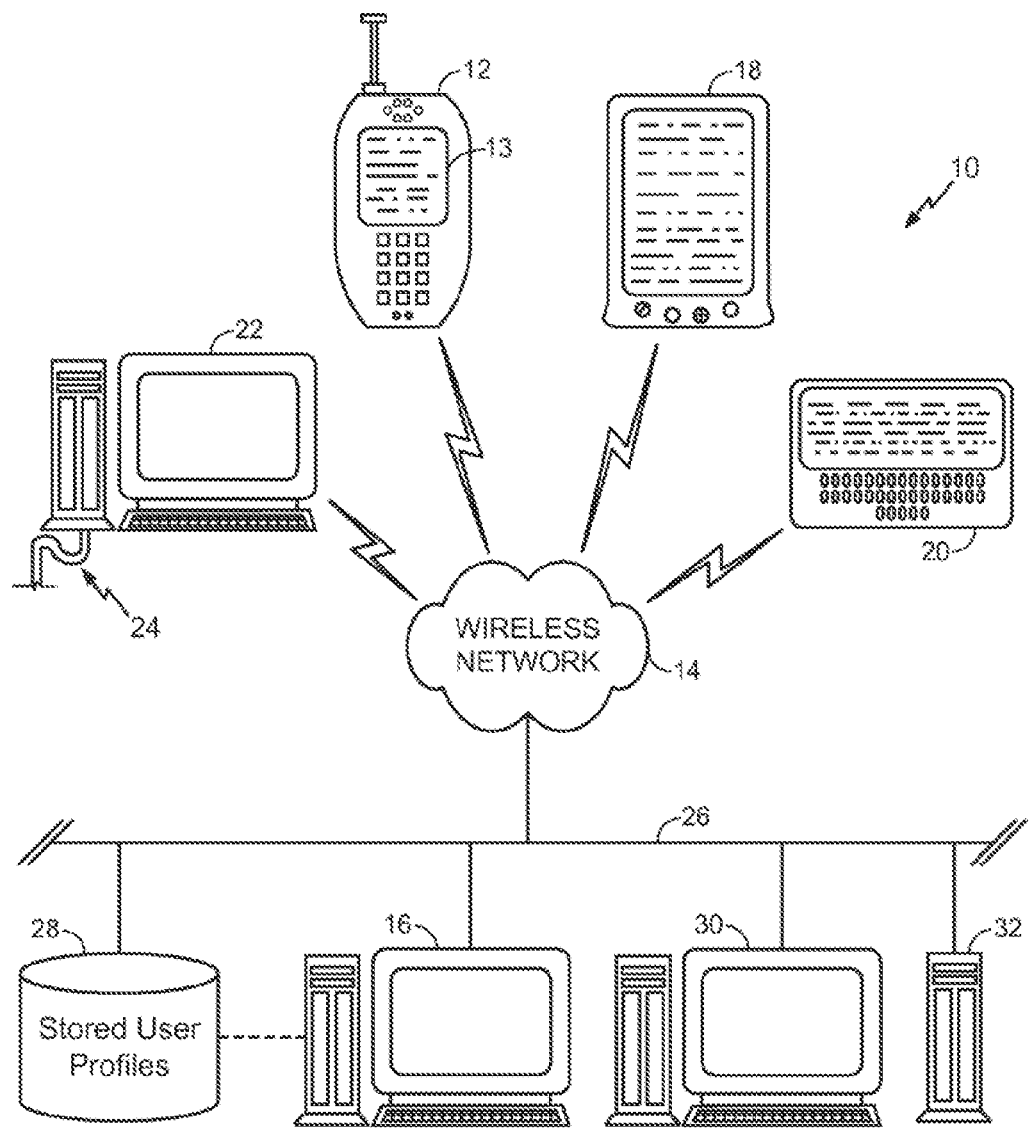
FIG. 1 is one embodiment of an architecture of a wireless communication network with a plurality of wireless communication devices communicating thereacross.

FIG. 1 illustrates one embodiment of the present inventive system 10 that allows wireless communication devices, such as mobile telephone 12, in communication across a wireless network 14, with other computer devices, such as a user profile server 16, that selectively interacts with the wireless devices 12, 18, 20, 22 across a wireless communication portal or other data access to the wireless network 14 to gather user data from the devices 12, 18, 20, 22 and generate and return user profiles to the devices 12, 18, 20, 22 and can store user profiles in user profile database 28. Other computer devices, such as an application server 30 and storage 32 can be available to the wireless communication devices 12, 18, 20, 22 either exclusively or in parallel to interaction with the user profile server 16 and resident on other networks, such as a local area network (LAN) 26.

As shown here, the wireless device can be a cellular telephone 12, with a graphics display 13, a personal digital assistant 18, a mobile email device 20 with a graphics display, which is shown here as a wireless device with qwerty capability such as a Blackberry® by RIM, or even a separate computer platform 22 that has a wireless communication portal, and may otherwise have a wired connection 24 to a network or the Internet. The system 10 can thus be performed on any form of remote computer module including a wireless communication portal, including without limitation, wireless modems, PCMCIA cards, access terminals, personal computers, access terminals, telephones without a display or keypad, or any combination or sub-combination thereof. Further, the term "application" as used herein is intended to encompass executable and nonexecutable software files, raw data, aggregated data, patches, and other code segments.

Figure 3:
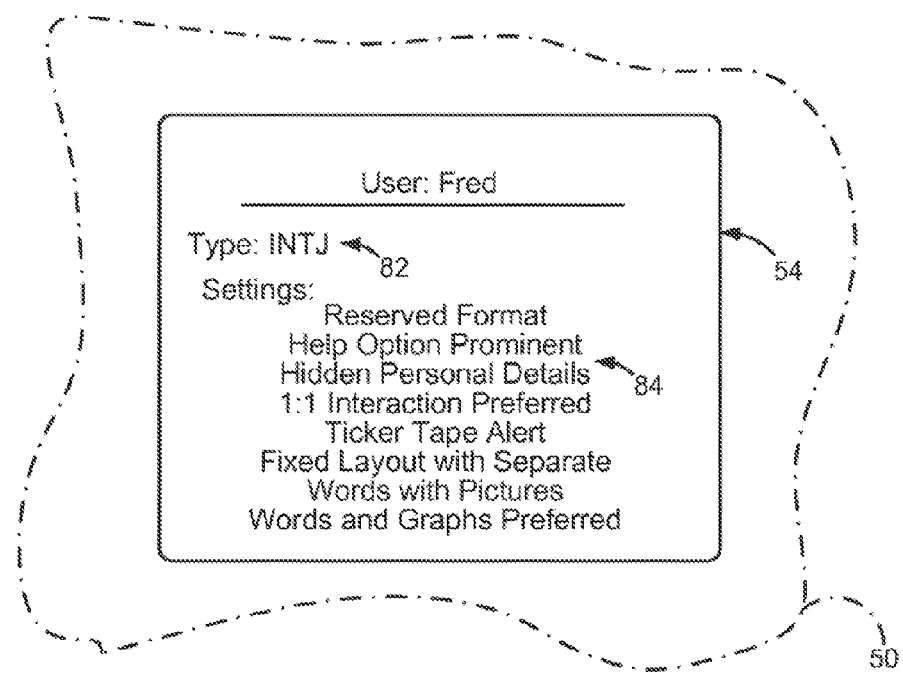
FIG. 3 is a screen shot for the display of the wireless communication device illustrating a personality profile for a user of the device.
Figure 4:
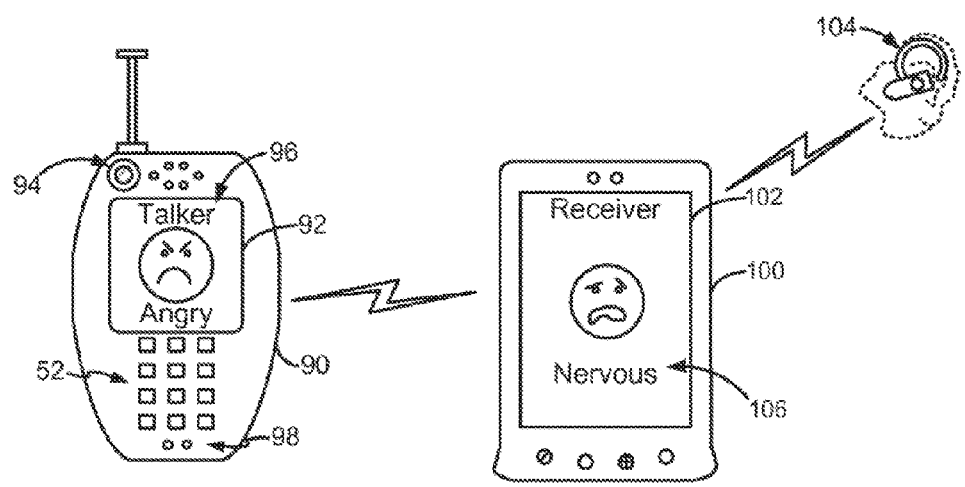
FIG. 4 is a representative diagram illustrating one embodiment of the invention wherein two communicating devices are showing the short-term emotional profile for the user of the other wireless communication device.

In overview, the system 10 allows the wireless communication devices 12, 18, 20, 22 to alter their functionality based upon a specific user profile generated from the user of the wireless communication device 12, 20, 22. The system 10 also enables the wireless communication devices 12, 18, 20, 22 to create user profiles for other users during interaction with other wireless communication devices. As is more fully described below, at least one wireless communication device 12, 18, 20, 22 is configured to gather user data from physical user interaction with the wireless communication device 12, 18, 20, 22, wherein the wireless communication device has a functionality for user interaction, such as a specific UI as shown in FIGS. 3 and 4. In this embodiment of the system 10, the wireless communication device 12, 18, 20, 22 selectively transmits the gathered user data across the wireless communication network 14 to, at least, the user profile server 16, which is configured to receive the transmitted gathered user data, and which creates user profile data (such as a personality profile as described herein) based upon the received gathered user data. The user profile server 16 transmits the user profile data to the sending wireless communication device 12, 18, 20, 22, and the wireless communication device 12, 18, 20, 22 can alter wireless communication device functionality based upon the received user profile data. As shown further below, the user profiling can also occur completely at the wireless computer device 12, 18, 20, 22.

Figure 2:
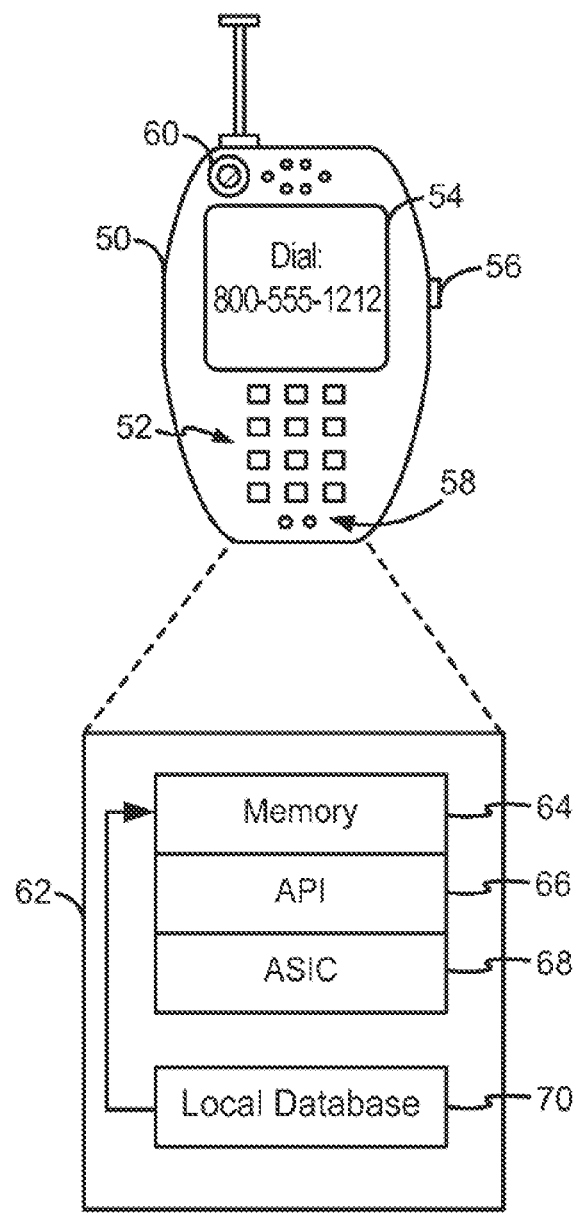
FIG. 2 is an representative diagram illustrating a mobile telephone as a wireless communication device, with a block diagram of the resident computer platform.

As particularly shown in FIG. 2, the wireless communication device, as embodied here is a mobile telephone 50 having a computer platform 62. The mobile telephone 50 has a numeric keypad 52, a graphic display 54 through which is implemented a user interface (UI), a microphone 58, and a group communication activator, or here, a push-to-talk button 56, and a camera 60. There are other devices and components known in the art that can be placed on the wireless communication computer platform 62 and utilized by the user and/or the computer platform 62 of mobile telephone 50.

The computer platform 62 can receive and execute software applications transmitted from the application download server 30. The computer platform 50 includes, among other components, an application-specific integrated circuit ("ASIC") 68, or other processor, microprocessor, logic circuit, programmable gate array, or other data processing device. The ASIC 68 is installed at the time of manufacture of the wireless device and is not normally upgradeable. The ASIC 68 or other processor executes an application programming interface ("API") layer 66 that interfaces with any resident programs in the memory 64 of the wireless device. The memory can be comprised of read-only or random-access memory (RAM and ROM), EPROM, EEPROM, flash cards, or any memory common to computer platforms. The computer platform 62 also includes a local database 70 that can hold the software applications not actively used in memory 64, such as the software applications downloaded from the application download server 30. The local database 70 is typically comprised of one or more flash memory cells, but can be any secondary or tertiary storage device as known in the art, such as magnetic media, EPROM, EEPROM, optical media, tape, or soft or hard disk. The user profiling can therefore be held in the local database 70 and implemented on the computer platform 62 when required.

In general, mobile telephones and telecommunication devices, such as cellular telephone 50, are being manufactured with increased computing capabilities and are becoming tantamount to personal computers and hand-held personal digital assistants ("PDAs"). These "smart" cellular telephones allow software developers to create software applications that are downloadable and executable on the processor, such as ASIC 68, of the cellular device. The downloaded data or executed applications can be immediately displayed on the display 54 or stored in the local database 70 when not in use. Likewise, the application can execute automatically or transparently to the user. The software applications can be treated as a regular software application resident on the wireless device 12, 18, 20, 22, and the user can selectively upload stored resident applications from the local database 70 to memory 64 for execution on the API 66. The user of the wireless device 12, 18, 20, 22 can also selectively delete a software application from the local database 70. As a result, end-users of the mobile telephones 50 can customize their telephones with programs, such as games, printed media, stock updates, news, or any other type of information or program available for download from application download servers through the wireless network 14.

In operation, the wireless communication devices 12, 18, 20, 22 gather user data either directly from the user from interaction, such as asking the user a series of questions and/or can make observations of the user and interpret the data, such as through sensing devices like the camera 60 and microphone 58. The wireless communication device 12, 18, 20, 22 can also collect data about the user from another device, such as user profile server 28, or wireless communication device 12, 18, 20, 22, via direct connection or through the internet. The user data is preferably collected and updated periodically for the purpose of generating a user profile, such as a personality profile, a psychological type, a medical diagnosis, or an emotional state. The user profile can be for the "short-term," such as for user data gathered in a current communication or can be "long-term," or based upon a history of user interaction. The user profile can be used in supplement with other configuration data to deliver a user experience which would be most compatible, entertaining, and productive for the end user of the wireless communication device 12, 18, 20, 22. As used herein, the term "physical interaction" is meant to encompass the range of user interaction, such as physical contact with the device buttons, keypad 52, and other direct contact, and can also encompass data sensed from the user by the wireless device 12, 18, 20, 22, such as pictures taken from the camera 60, or medical information taken from a medical device, such as remote earpiece 104, voice volume, speech patterns, and the like.

As an example, a wireless communication device, such as mobile phone 50, has the ability to support multiple UI configurations and have multiple possible dialogs, functions, applications and contexts within those configurations. The mobile phone 50 could either recognize the user thereof via user input, such as a PIN number, use biometric data, such as a fingerprint reader, voice pattern recognition or face recognition (microphone 58, camera 60), or request identification of the user. The device would present the user with visual and verbal UI clues for its use that are compatible and harmonious with the user's personality (such as the UI configurations illustrated in FIG. 5). The wireless computer device 12, 18, 20, 22 will perform specific applications or behaviors based on the personality of the user in addition to more common UI behaviors. The mobile phone 50 can therefore leverage applications for the user that are compatible and harmonious with the user's personality and any situational data (inputs from the camera 60, microphone 58, or any other sensors). The wireless communication device 12, 18, 20, 22, can also be directly in communication with the user profile server 16, thus having significant resources available to generate many types of profiles or scores to be leveraged by the user interface or other device functionality, such as a personality score, an Intelligence Quota (IQ) score, cultural score, and religion score.

Other computer devices, such as wireless communication devices 12, 18, 20, 22, user profile server 16 or other devices on the wireless network 14, and applications on those devices that are connecting to the wireless communication device 12, 18, 20, 22 that stores a user profile, can selectively have access to the user profile in order to aid the calling party or application to communicate better with the user. The permission to access the data can be limited by the system 10, or only permissible through user allowance.

There are several personality tests known that give one insight into the behavior of a person, and the system 10 and wireless devices 12, 18, 20, 22 can individually or in tandem take gathered user data and execute a personality test on the user to try to determine user preferences and behavior. For example, one well known personality test is the "Myers Briggs" personality test. In simple overview, there are four categories of personality that are tested and evaluated. The first is "introversion" and "extroversion". These attitudes show how a person orients and receives their energy. In the extroverted attitude the energy flow is outward, and the preferred focus is on other people and things, whereas in the introverted attitude the energy flow is inward, and the preferred focus is on one's own thoughts and ideas.

Another attitude is "sensing" and "intuition," which are the perceiving functions. They indicate how a person prefers to receive data. Sensing prefers to receive data primarily from the five senses, and intuition prefers to receive data from the unconscious, or seeing relationships via insights. A third attitude is "thinking" and "feeling," which are the judging functions. Thinking uses logical "true or false," if-then logical connections. Feeling uses "more or less, better-worse" evaluations. When Thinking or Feeling is extroverted, judgments tend to rely on external sources and the generally accepted rules and procedures. When introverted, Thinking and Feeling judgments tend to be subjective, relying on internally generated ideas for logical organization and evaluation. The fourth attitude is "judging" and "perceiving," which reveal the specific attitudes of the functions. Judging types tend to prefer a step-by-step approach to life, relying on external rules and procedures, and preferring quick closure. The perceiving function is the direct opposite to the judging function. This can result in a "bouncing around" approach to life, relying on subjective judgments, and a desire to leave all options open. The four attitudes can be placed into a chart, like that shown in FIG. 5, and the wireless communication device 12, 18, 20, 22 can accordingly set the device functionality based upon what personality the user is believed to be. The chart in FIG. 5 thus contains device UI predetermined settings for all potential 16 Myers Briggs personality types.

As shown in the example of FIG. 3, the display 54 of the mobile phone 50 can show the determined user profile for the user of the mobile phone 50, which here is the Briggs Myers personality evaluation, to the user. The user has been determined to be an INTJ, shown at arrow 82, with the device functionality set accordingly, as shown at arrow 84 (Box 86 in FIG. 5). This user profile can be based upon long-term user interaction with the wireless communication device 12, 18, 20, 22, or can be updated in the short-term, such as in the conversation shown in FIG. 4. Likewise, the same user profile can be generated for another user of a communication device, such as shown and described below relative to FIG. 8.

In FIG. 4, an active communication is occurring between mobile phone 90 and mobile wireless platform 100 where the emotion of the speakers engaged in a conversation is profiled and the profile is communicated to the other device such that the users of the devices know what the emotional state of the other user is. The mobile phone 90 includes a display 92, and a camera 94. The mobile wireless platform 100 includes a display 102 and also a remote earpiece 104. In this embodiment, the remote earpiece 104 also includes a medical diagnostic device that senses the blood pressure of the wearer (user). The user profiling in this communication typically occurs in the short-term in this embodiment, virtually in real time because emotions are being profiled. Here the receiving device is the mobile phone 90, and the talker, mobile wireless platform 100, is indicated as being angry which is shown on the mobile phone 90 in graphic 96. Here, the indication of anger comes from the blood pressure data taken from the user at remote earpiece 104, and the mobile wireless platform 100 sends the angry profile to the mobile phone 90.

In parallel, the mobile phone 90 gathers user data from the microphone 98 from the user who is speaking and the voice can be analyzed to indicate stress, which implies nervousness. The nervousness profile is then sent from the mobile device 90 to the mobile wireless platform 100. The receiver is then indicated as nervous on the display 102 of the mobile wireless platform 100, as shown at graphic 106. Such a presentation can be done in split-screen such that the user of the device sees both the profile being sent to the other device and the profile from the other device.

The gathering of user data can therefore be based upon interpretation of short-term data input by the user into the wireless communication device, such as the volume of the voice of the speaker, the pressure the user uses to press the keys (such as at keypad input 52 in FIG. 2), and a picture of the user (such as at camera 60). If the wireless communication device 12, 18, 20, 22 includes a medical diagnostic device, such as the remote earpiece 33 in FIG. 4, the short-term profile can be a medical diagnosis or other emotion or personality profile based upon gathered medical data. The gathering of short-term user data can also be based upon interpretation of data input by the user into the wireless communication device 12, 18, 20, 22, such as a direct questionnaire of the user.

The gathering of user data can also be based upon long-term user interaction with the wireless communication device 12, 18, 20, 22. For example, the gathering of user data can be based upon interpretation of a contact list resident in the wireless communication device 12, 18, 20, 22, or the interpretation of the number of members of one or more communication groups for the wireless communication device. Accordingly, a large number of contacts or group communication members would indicate extroversion in terms of the Myers Briggs personality test. The long-term interaction of the user with the wireless communication device 12, 18, 20, 22 can be based upon any gathered data gathered in the short-term that is averaged to better determine the profile of the user. As described below, the short-term comparison and long-term comparison user profile can be compared to either help to aid in the short-term profile, e.g. if the user always shouts, shouting in the short-term should not indicate anger.

Figure 6:
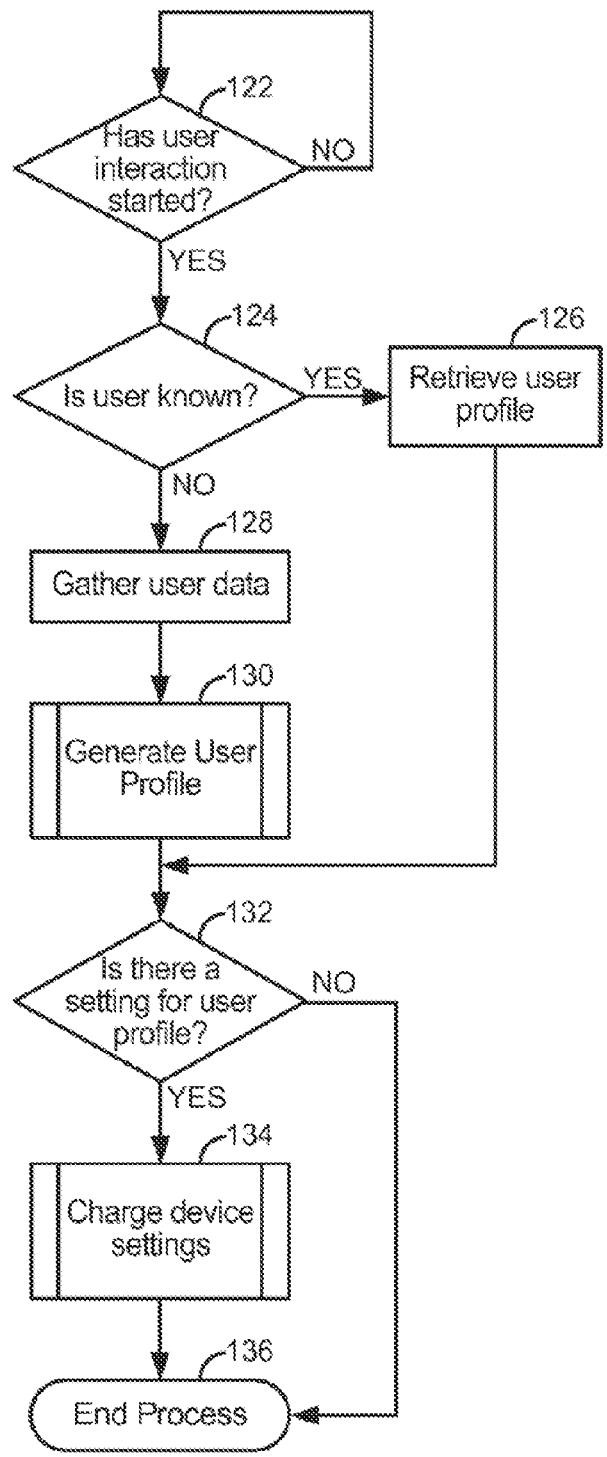
FIG. 6 is a process flow diagram illustrating one embodiment of the method to generate a user profile and change settings in accordance therewith at a wireless communication device.

In one embodiment shown in FIG. 6, the wireless communication device 12, 18, 20, 22 executes a method on the computer platform 62 thereof such that a user profile can be generated locally for a user. A determination is made, as shown at decision 122, as to whether the user interaction with the wireless communication device 12, 18, 20, 22 has started. If not, a wait state is entered until user interaction starts. Otherwise, if user interaction has started at decision 122, a determination is then made as to whether the user is known, as shown at decision 124. If the user is known at decision 126, the user profile is retrieved, as shown at step 126. Otherwise if the user is not known at decision 124, the user data is gathered, shown at step 128, and the user profile is generated, as shown at predefined process 130, which can be a personality profile, emotional state, medical profile, and the like. Then a determination is made as to whether there is a user profile setting for the wireless device based upon the user profile, as shown at decision 132. Decision 132 is also reached if a user profile was retrieved at step 126. If there is not a setting for the user at decision 132, then the process ends, as termination 136. Otherwise, if there is a setting for the user profile at decision 132, the wireless communication device 12, 18, 20, 22 settings are changed, as shown at predefined process 134, and then the process ends at termination 136.

Figure 7:
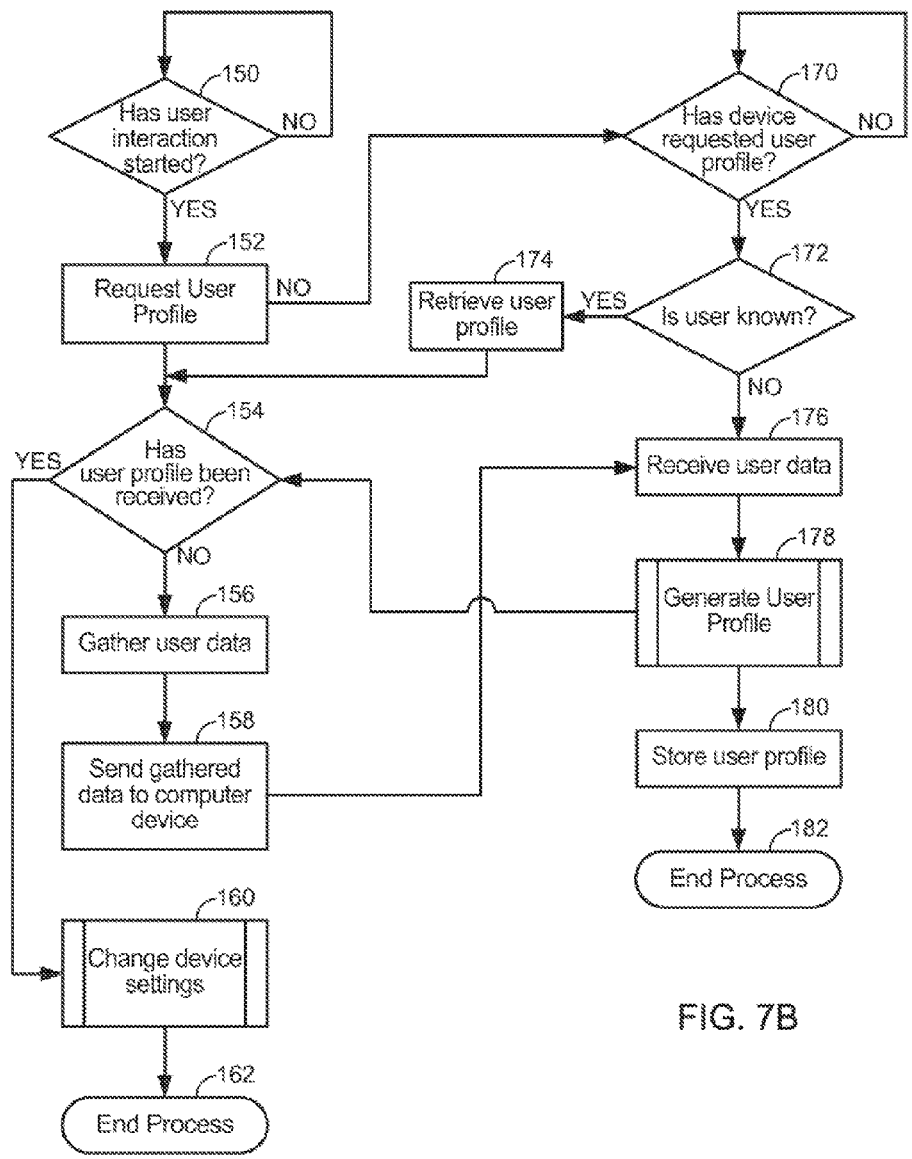
FIG. 7A is a process flow diagram of an embodiment method for sending gathered user data from a wireless communication device to another computer device executing a process shown in FIG. 7B, to receive a user profile back from the other computer device.
FIG. 7B is a process flow diagram of an embodiment method for creating and storing user profiles at a computer device based upon the gathered user data sent from the wireless communication device in FIG. 7A, and then sending user profiles back to the wireless communication device.

FIGS. 7A and 7B is illustrate one embodiment of a method for sending user data from a wireless communication device 12, 18, 20, 22 to another computer device, such as user profile server 16, which is executing the process shown in FIG. 7B, to receive a user profile back from the other computer device. The wireless communication device 12, 18, 20, 22 determines an interaction with a user of that device has started, as shown at decision 150. This can be the user unlocking the phone with a pin, or starting to interact with the device functionality such as choosing a contact to dial or a PTT group to make a group call to. If no user interaction has started at decision 150, a wait state is entered until user interaction begins. If user interaction has started at 150, the wireless communication device 12, 18, 20, 22 requests a user profile for the user from the user profile server 16, which will enter the process shown in FIG. 7B. The user is preferably determined with some specificity, such as being identified based upon pin entry, picture taken, voice capture, and the like, but the process could simply assume the identity of the user, such as assuming the user is the owner of the wireless communication device 12, 18, 20, 22, or the last user.

The process in FIG. 7A on the wireless communication device 12, 18, 20, 22 then makes a determination as to whether a user profile has been received for the user, as shown at decision 154. If a user profile has been received at decision

154, then the wireless device functionality settings are changed, as shown as predefined process 160, such as changing the UI, screen presentation, device volume, and the like, and the process then ends at termination 162, and the wireless communication device 162 will await another user interaction at decision 162. If a user profile has not been received at decision 154, then the wireless communication device 12, 18, 20, 22 gathers the user data (as described in the various embodiments herein) and sends the gathered user data to the user profile server 16, as shown at step 158, and enters a loop at decision 154 to gather and send user data until ultimately receiving a user profile back from the user profile server 16.

In FIG. 7B, the process at the user profile server 16 in communication with the wireless communication device 12, 18, 20, 22 is shown. The user profile server 16 determines if the wireless communication device 12, 18, 20, 22 has requested a user profile, as shown at decision 170, and if no request has been made, the user profile server 16 will enter a wait state for the request at decision 170. Otherwise, once the user profile has been requested at decision 170, a determination is then made as to whether the user for which the user profile is requested is known, as shown at decision 172. If the user is known, the user profile is retrieved, as shown at step 174 and then sent back to the wireless communication device 12, 18, 20, 22. Otherwise, if the user is not known to the user profile server 16 at decision 172, the user profile server 16 will not send a user profile to the wireless communication device 12, 18, 20, 22 which will cause that device to start gathering and sending user data as shown in FIG. 7A, and the user profile server 16 will receive gathered user data, as shown at step 176, and then generate a user profile for the received user data, as shown as predefined process 178. The user profile server 16 then sends the generated user profile back to the wireless communication device 12, 18, 20, 22, and also stores the user profile, as shown at step 180, and the process then ends as shown at termination 182. The storage of the generated user profile, step 180, is preferable to create a database of user profiles, but is not required.

Figure 8:
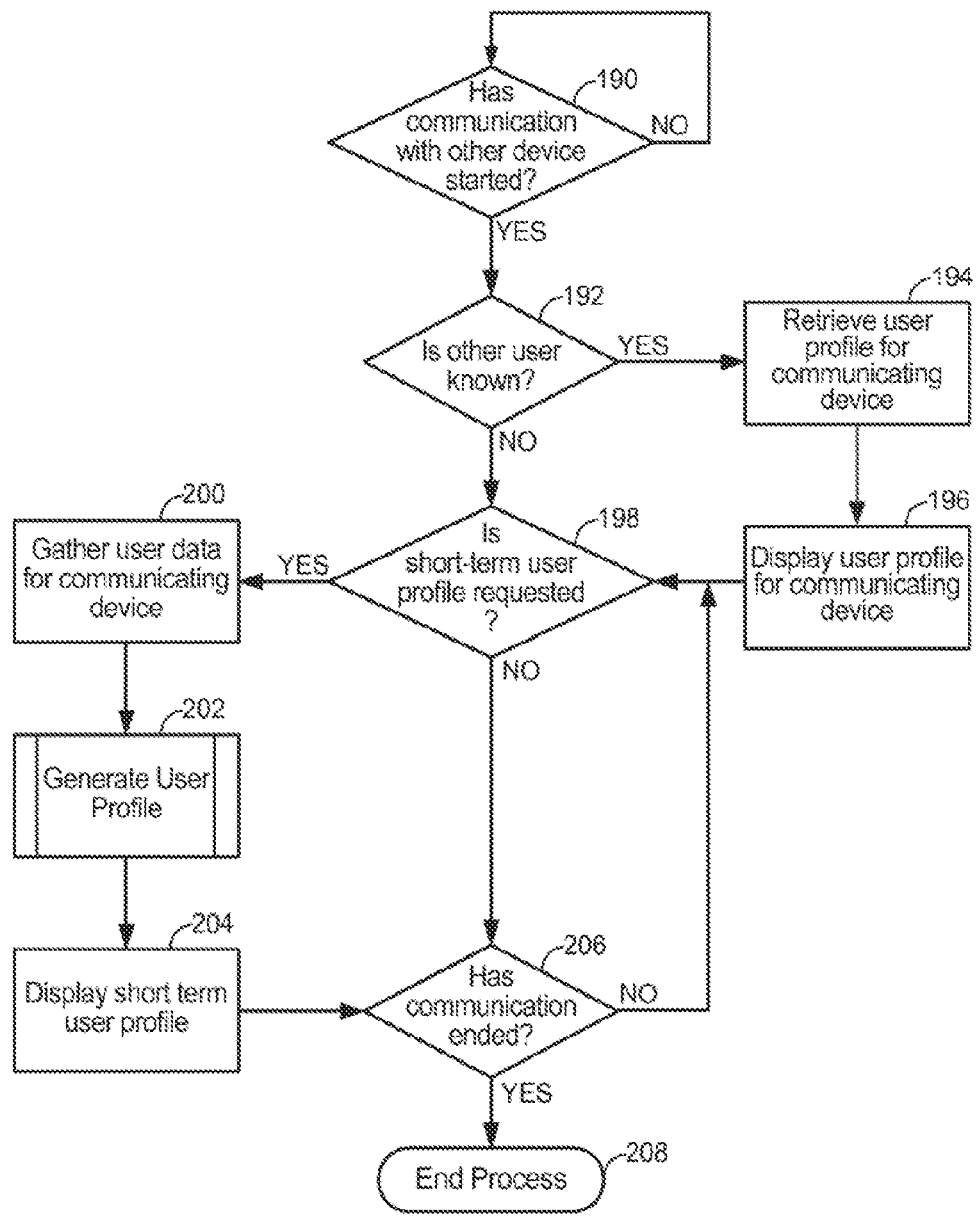
FIG. 8 is a process flow diagram of an embodiment method executing on a wireless communication device that allows either a stored user profile to be shown for the user of a communicating device, or a short-term profile can be alternately generated and displayed.

FIG. 8 is a flowchart for one embodiment of the method executing on a wireless communication device 12, 18, 20, 22 that allows either a stored user profile to be shown for the user of a device communicating with that wireless communication device 12, 18, 20, 22, or a short-term profile can be alternately generated and displayed, such as in the wireless communication devices 90 and 100 in FIG. 4, which are in engaged in a communication. The wireless communication device 12, 18, 20, 22 determines if a communication with another device has started, as shown at decision 190, and if no request has been made, the wireless communication device 12, 18, 20, 22 will enter a wait state for the communication to start at decision 176. Otherwise, once the communication has started at decision 190, a determination is then made as to whether the user for the other communication device is known, as shown at decision 192. If the user is known, the user profile for the other user is displayed, such as on display 92 of mobile phone 90, as shown at step 196. Otherwise, if the user is not known at decision 192, or after the user profile for the communicating user is displayed (step 196), a determination is then made as to whether a short-term profile of the other user is requested, as shown at decision 198.

If no short-term profile is requested at decision 198, a determination is then made as to whether the communication has ended, as shown at decision 206. Otherwise, if a short-term profile is requested by the user of the wireless communication device 12, 18, 20, 22 at decision 198, the user data is gathered for the communicating device, as shown at step 200, which can be data such as the caller's voice, a picture of the caller, and other medical data sent as described herein, or can alternately be the review of a specific user profile sent from the communicating device. Then a short-term user profile is generated, as shown at predefined process 202, and the short term profile is displayed, such as on display 92 on mobile phone 90. The short-term profile can be an emotional state, like that shown in FIG. 4, or personality profile (such as Myers-Briggs type), psychological profile, or medical information. The predetermined process 202 can also include the retrieval of a long-term profile for the user and comparison of the long-term profile data with the short-term data to note any anomalies, e.g. such as shouting when the user always shouts or grimacing when the user always grimaces. Such harmonization data from the comparison can also be stored to make a more accurate long-term user profile.

After the short-term profile has been displayed at step 204, the determination as to whether that communication has ended, decision 206, is made. If the communication has not ended at decision 206, the process returns to decision 198 to determine if the short-term user profile is still requested, and then will update the short-term profile accordingly. Otherwise, if the communication has ended as decision 206, the process ends as shown at termination 208.

Other changes in the system 10 and methods shown herein will be apparent to those of skill in the art. For example, the method shown on the wireless communication device 12, 18, 20, 22 in FIG. 8 could likewise be implemented with a user profile server 16, similarly to the method shown in FIGS. 7A and 7B, but with the user profile server 16 supplying short-term user profiles to the wireless communication device 12, 18, 20, 22. Furthermore, more than two computer devices can be used in the present system and method, and accordingly, such implementation is readily scalable. And the wireless communication device 12, 18, 20, 22 could likewise show many communicating devices and their user profiles at once, such as in a group communication (PTT call).

It can be seen that the wireless device 12, 18, 20, 22 accordingly provides an inventive method of profiling a user of a wireless communication device 12, 18, 20, 22 and potentially altering the wireless communication device functionality based upon the user profile, through, in one embodiment, the gathering of user data from physical user interaction with the wireless communication device 12, 18, 20, 22, or alternately, the user data can come from another computer device in communication therewith, such as the user profile server 16. A user profile is then created as based upon the gathered user data, and the wireless communication device functionality altered based upon the gathered user data. Alternately, the user profile can be displayed to the user, such as shown in display 54 in FIG. 3.

The gathering of user data can based upon interpretation of short-term data input by the user into the wireless communication device 12, 18, 20, 22, as shown in FIG. 8, or alternately, can be based upon interpretation of long-term data input by the user into the wireless communication device 12, 18, 20, 22 over time, which can provide a more accurate user profile be eliminating anomalies in the data. The gathering of user data is based upon interpretation of user physical interaction with one or more data input mechanisms of the wireless communication device 12, 18, 20, 22, such as through speaking in the microphone 98, taking a picture through a camera 94, or even from a medical device, such as remote earpiece 104.

As discussed above, mobile communication devices (e.g., cellular phones, smart phones, tablets, etc.) have become faster and more feature-rich than ever, and are becoming tantamount to personal computers. Today's mobile devices have impressive processing capabilities, large memories, and include video cameras, GPS receivers, portable media players, sensors, and other similar components. In addition, mobile devices are now capable of executing powerful software applications, which may include productivity applications (e.g., email, calendar, contact databases, Microsoft® office, etc.), financial applications, social media applications (e.g., Facebook® app, etc.), and other applications for managing the user's personal and/or business life. Mobile devices may support cloud computing, wherein the mobile device may send and receive user information to and from a remote server such that the information is available everywhere and accessible on any compatible device (i.e., is independent of any specific device).

Due to these enhancements, mobile devices are rapidly growing in use and in popularity. Mobile devices are quickly becoming a necessary and indispensable tool for navigating modern society, conducting business, interacting with others, and accomplishing many everyday tasks. Accordingly mobile devices are becoming ubiquitous and ever-present in modern life. As such, mobile devices now have unprecedented levels of access to information generated by, or relating to, mobile device users. Also, mobile devices are being equipped with more and different types of radios, enabling wireless communications with a variety of devices, including equipment that may obtain information about a user (e.g., exercise equipment, medical monitors, automobiles, kitchen appliances, points-of-purchase in stores and gas stations, etc.). In various embodiments, this information may be used to generate user profiles that more accurately characterize the user.

With such access to other information related to a user, further embodiments may includes systems, methods, and devices for altering the functionality of another mobile device based upon a user profile generated from such other information available to the communications device. Various embodiments may thus make use of such information in addition to or in combination with the above mentioned techniques for altering a functionality of a wireless communication device based upon a user profile generated from data gathered from a physical user interaction. The information may be collected from software applications (e.g., calendar application, browser, etc.), geo-spatial positioning and navigation systems (e.g., global positioning system or "GPS"), personal monitoring devices (e.g., heart rate monitor, blood pressure monitor, thermometer, pedometer, blood glucose meter, exercise equipment, etc.) and/or other sensors (e.g., humidity sensor, breathalyzer, galvanic skin response sensor, etc.). Personal monitoring devices and other sensors may be a part of the wireless communications device or may be separate devices in communication with the wireless communications device (e.g., external sensors, etc.). The information from these sources may be collected from or stored on the wireless communication device, another wireless communication device, a server, the Internet (e.g., in "the cloud"), or any combination thereof. In an embodiment, the user profile may be generated from a combination of information gathered from a physical user interaction and other information available to the device.

In an embodiment, the information used to generate the user profile may be information collected from software applications on the user's communication device. In various embodiments, such software applications include but are not limited to: calendar and reminder applications; financial applications; applications for accomplishing specific tasks (e.g., word processing, preparing tax reforms, presentation applications, or accounting applications); location based applications (e.g., mapping and geolocation apps); web browsers; entertainment applications (e.g., an audio or multimedia player application); applications for accessing user accounts (e.g., banking apps); and person training and development applications. As with embodiments that develop a user profile based on interactions with the mobile device, these embodiments may infer activities, moods, availability and other useful profile information based on the information available from applications and data stores on the mobile device, either alone or in combination with information gathered from user interactions with the mobile device.

For example, the user profile may be generated to account for the user's schedule, using information obtained from the user's calendar application (e.g., currently in a meeting, meeting this afternoon, is in meetings all day, has meetings with important clients, etc.). Likewise, the user profile may be generated to account for how busy the user is by evaluating the types of applications being used (e.g., using tax preparation software vs. games or social media).

Other information available on the mobile device that may be used to generate the user profile may include the number and content of communications. For example, a large number of social media status updates may indicate that user is not busy, or the presence of an uncharacteristically large number of negative words in emails may indicate user is upset or angry.

Other information available on the mobile device that may be used to generate the user profile may include financial information. For example, if the user's bank account balance (or stock portfolio) recently increased by a significant amount, this may indicate that the user is more likely to be in good mood, whereas a significant decrease (or a prolonged reduction) may indicate that the user is likely to be upset or under elevated levels of stress.

Other information that may be used to generate the user profile may include browsing information (e.g., past searches, browsing history, types of websites visited, content of websites visited, etc.).

In an embodiment, mobile device location information may be used to generate the user profile, alone or in conjunction with user interactions with the device and/or other information available to or within the device. For example, the user's current location may be determined using a GPS receiver in the phone (or other similar positioning technologies of the Mobile device), and cross referenced with a map, a database or user information to determine if to determine if the user is currently at home, work, school, theater, restaurant, etc. This information may be used, for example, when determining the user's mood, psychological type, emotional state, or in making a medical diagnosis. For example, the user may be more likely to be in a pleasant mood if he/she is at home, or more likely to be annoyed if receiving a phone call while at a restaurant. Again, various embodiments may use location information in conjunction with other information collected from the user (e.g., financial information, mobile device activity, etc.) to generate the user profile.

In addition to the user's current location, the location information may include information regarding the user's current movements (e.g., is currently traveling, is exercising, is stationary, etc.) and/or history of movements (e.g., was in Baltimore last week, has been traveling extensively, etc.). In an embodiment, the profile may be generated by taking into account whether the user is following his/her established routine (e.g., arrived to work on time, still at work) or is off his/her routine (e.g., arrived later than usual, left earlier than usual). This information may be used, for example, in conjunction with other information to determine whether the user is experiencing a medical condition, or is dealing with a personal emergency that could impact the user's mood, emotional state, or medical diagnosis.

In an embodiment, information obtained from the media player may be used to generate the user profile. For example, if the user is listening to positive or upbeat music, it may indicate that he/she is more likely to be in a good mood. As another example, if the user's listening history indicates that the user has been recently listening to uncharacteristically sad or low tempo music, this may indicate that the user is more likely to be sad or in a poor emotional state. As another example, if the user is watching a movie, it may indicate that he is either available or busy, depending on the content of the movie, the user's viewing history, the user's personality (e.g., information obtained from sources), etc.

In a further embodiment, the user profile may be generated based at least in part on information obtained from personal monitoring devices (e.g., heart rate monitor, blood pressure monitor, thermometer, pedometer, blood glucose meter, etc.) that are either a part of (e.g., embedded, connected via USB, etc.), or in communication with (e.g., BlueTooth®, WIFI, 3G, etc.), the mobile device. For example, information obtained from a heart rate monitor, blood glucose meter and/or blood pressure monitor may be used to determine if the user is exercising (and therefore occupied), experiencing a medical condition, under stress, or in a bad mood, etc.

In an embodiment, the user profile may be generated based on information obtained from other types of sensors (e.g., humidity sensor, breathalyzer, galvanic skin response sensor, etc.) that are either a part of, or in communication with, the mobile device. For example, high humidity information obtained from a humidity sensor may indicate that the user is likely to be irritated. Information obtained from a breathalyzer may be used to infer that the user is experiencing a medical condition or has been drinking alcohol, which may identify the user's emotional state or mood.

Figure 9:
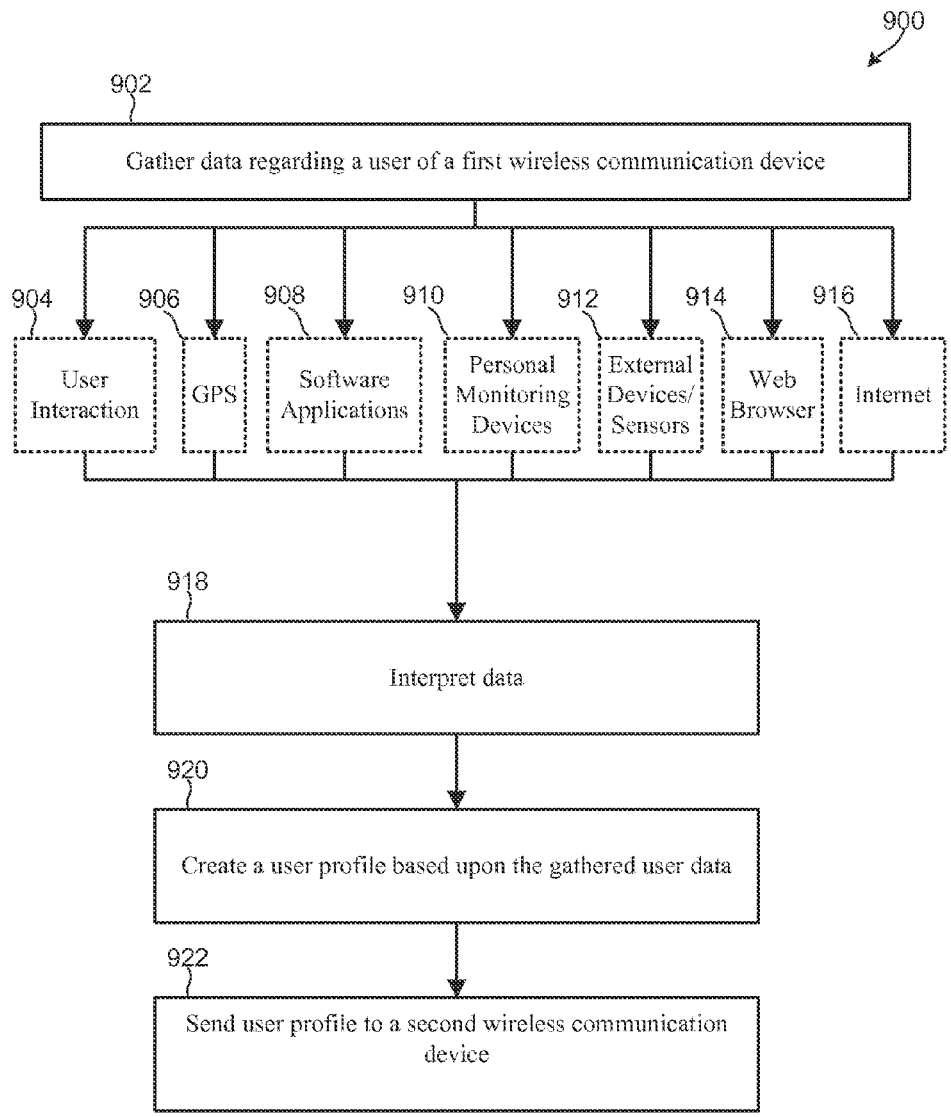
FIG. 9 is a process flow diagram of an embodiment method for gathering data regarding a user of the communication device to generate a user profile.

FIG. 9 illustrates an embodiment method that may be implemented on a mobile communication device for gathering data regarding a user in order to generate a user profile on the communication device. In step 902, a first communication device may gather information regarding the user of the first communication device. Such user information may be collected from a user interaction in optional step 904 (e.g., physical contact with the device buttons, etc.), geo-spatial positioning and navigation systems within the communication device in optional step 906, software applications running on or that have been run on the communication device in optional step 908, personal monitoring devices in optional step 910, external devices and/or other sensors in optional step 912, a web browser on the communication device in optional step 914, and/or from the Internet or other network in optional step 916. The information from some or all of these various sources may be collected from or stored on the first wireless communication device, attached devices (e.g., heart rate monitor, etc.), another wireless communication device, a server, the Internet (e.g., in "the cloud"), or any combination thereof.

In step 918, the first communication device may interpret the gathered data to obtain information that may useful in creating a user profile. This interpretation of the gathered data will depend upon the type and format of the information. Some examples will serve to illustrate the types of data interpretation that may be accomplished in step 918 depending upon the type of information.

When the gathered data is obtained from a calendar or user schedule application, the data may be interpreted to identify a user's scheduled appointment, recent appointments, and/or future appointment, any of which may reflect on the user's activities, moods, etc.

When the gathered data is related to applications in use or recently used by the user, the data may be interpreted in order to identify the types of software applications that the user is running, which may reflect on the user's current activities, workload, and mood. For example, if the user has been recently running game applications, it may indicate that the user is in a good mood or has time available for conversation.

When the gathered data is obtained from communication applications, such as messaging and/or e-mail applications, the data may be interpreted to determine characteristics related to the communications. For example, the interpretation may look for words expressing anger or urgency, count the number of !, and/or use language interpreting algorithms to assess the emotional content of the communications.

When the gathered data is obtained from a social media application, the data may be interpreted in order to assess a user's activities or the nature of the interactions with others, which may be indicative of current activities or moods.

When the gathered data involves financial information related to the user, the data may be interpreted to determine whether the user has a large or small bank account, since such financial information may be reflective of the user's mood.

When the gathered data is obtained from a web browser, the data interpretation may include inferring a user's mood or activities based on a history of Internet searches, types of websites accessed and/or content downloaded from websites.

When the gathered data relates to a current location (e.g., movement, current GPS coordinates, etc.), the data interpretation may involve inferring a status or mood based upon the user's location. For example, if the gathered location data indicates that the user is currently in the Caribbean, this may indicate that the user is on vacation and in a good mood, but not receptive to business-related communications.

When the gathered data is obtained from a media player, the data interpretation may involve determining the type of media being played which may indicate a user's mood or openness to being interrupted. For example, if the user is listening to upbeat music, this may be interpreted as indicating that the user may be in a good mood and receptive to communications, whereas if the user is viewing a movie, this may indicate that the user is likely to be annoyed by an interruption until the movie is completed.

When the gathered data is obtained from a personal monitoring device (e.g., a heart rate monitor, a glucose meter, breathalyzer, etc.), the data interpretation may be as appropriate for that particular type of monitoring device, and may include using the data in a diagnostic algorithm, such as to estimate a user's current medical or physical condition.

When the gathered data is obtained from an external database, the data interpretation will depend upon the type of information obtained.

When the gathered data is obtained from a video camera, the data interpretation may involve analyzing a user's expression and/or movements to infer a mood or activity of the user.

In all of the data interpretations involved in step 918, the data interpretations may be related to physiological evaluations, emotional or mood evaluations, and/or medical diagnostic evaluations.

In step 920, the first communication device may generate a user profile based upon the gathered user data and/or data interpretations. In step 922, the first communication device may transmit the user profile to a second communications device, which may receive the user profile and alter its functionality as described herein.

Figure 10:
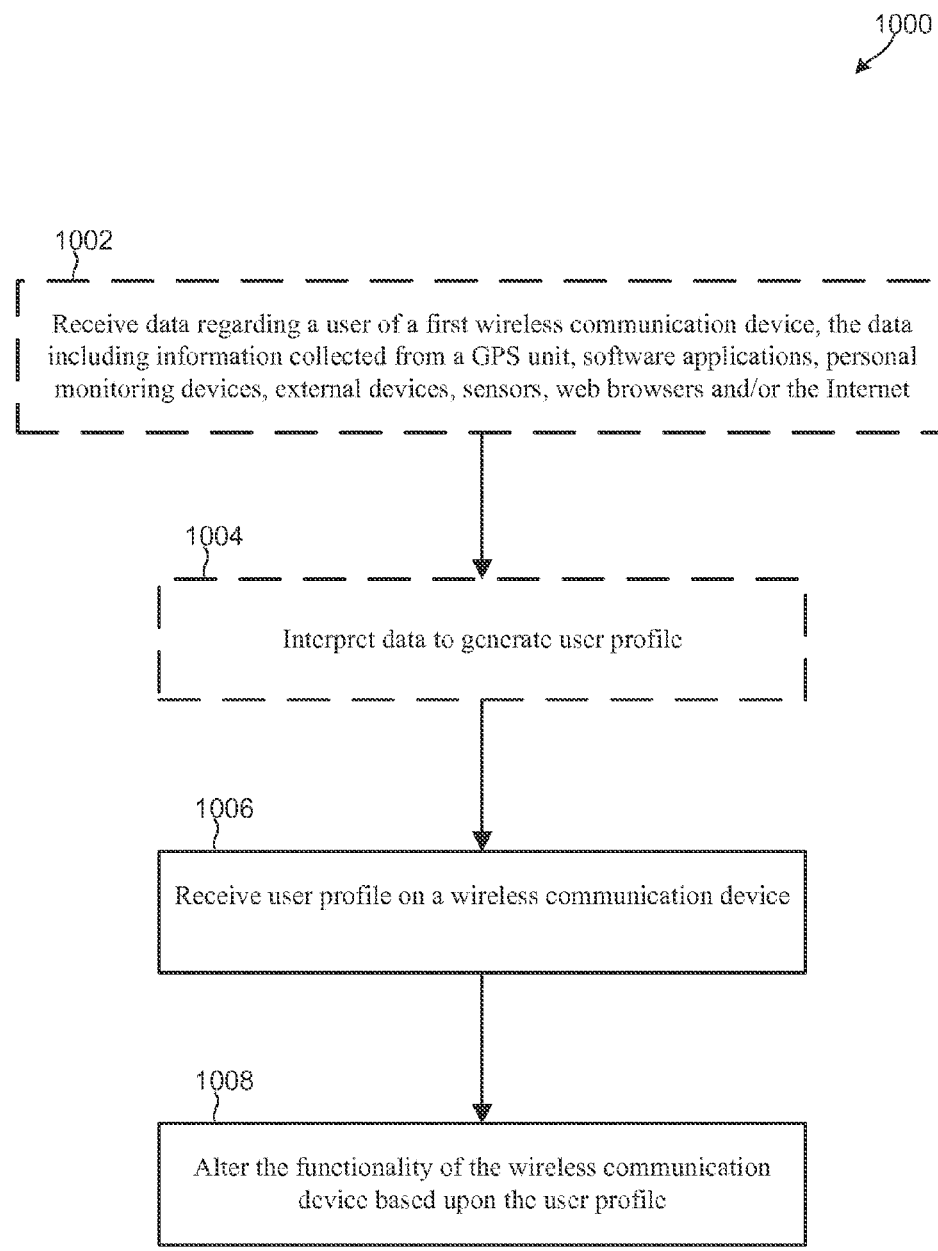
FIG. 10 is a process flow diagram of an embodiment method for receiving information for altering the functionality of a communication device.

FIG. 10 illustrates an embodiment method that may be implemented on a communication device for receiving information for altering the functionality of a wireless communication device. In optional step 1002, the communication device may receive data regarding a user of another wireless communication device. The received data may include information collected from a GPS unit, software applications, personal monitoring devices, external devices, sensors, web browsers and/or the Internet. In optional step 1004, the communication device may interpret the gathered data to generate a user profile. The interpretations of the received data may include any of the operations described above for step 918 with reference to FIG. 9. In step 1006, the communication device processor may receive the user profile, which may have been generated and stored in memory in step 1004, or generated on another communications device or a server (or a combination of another communications device and a server) and transmitted to the communication device. In step 1008, the communication device may alter its functionality based on the received user profile as described herein.

Figure 11:
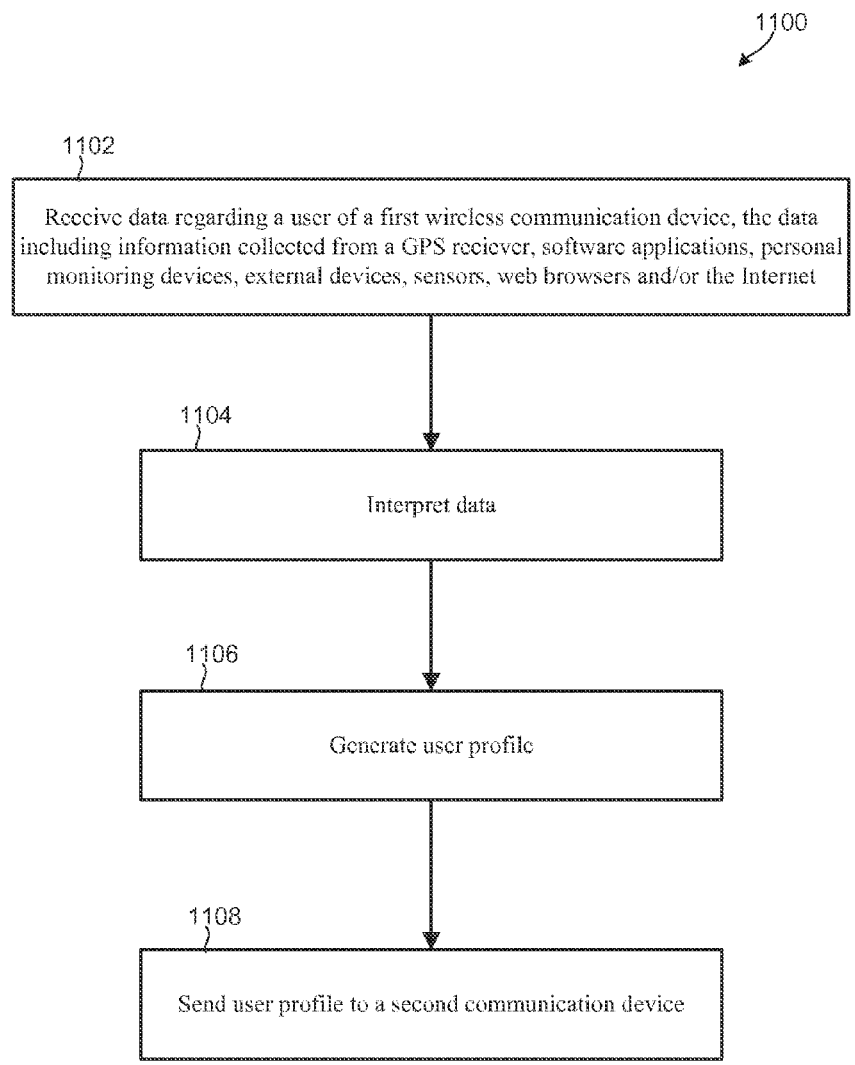
FIG. 11 is a process flow diagram of an embodiment method for receiving data regarding a user of a first wireless communication device to generate a user profile on a server and transmitting the generated user profile to a second wireless device.

FIG. 11 illustrates an embodiment method that may be implemented on a server for generating a user profile based upon data regarding the user received from a first wireless communication device, and transmitting the generated user profile to a second wireless device. In step 1102, the server may receive data regarding a user of a first wireless communication device. The received data may include information collected from a GPS unit, software applications, personal monitoring devices, external devices, sensors, web browsers and/or the Internet. In step 1104, the server may interpret the received data. The data interpretation accomplished in step 1104 may be similar to the data interpretations described above with respect to step 918 and reference to FIG. 9. In step 1106, the server may generate a user profile based on the received and interpreted data. In step 1108, the server may send the generated user profile to a second communications device in a format that enables the second communications device to alter its functionality.

Figure 12:
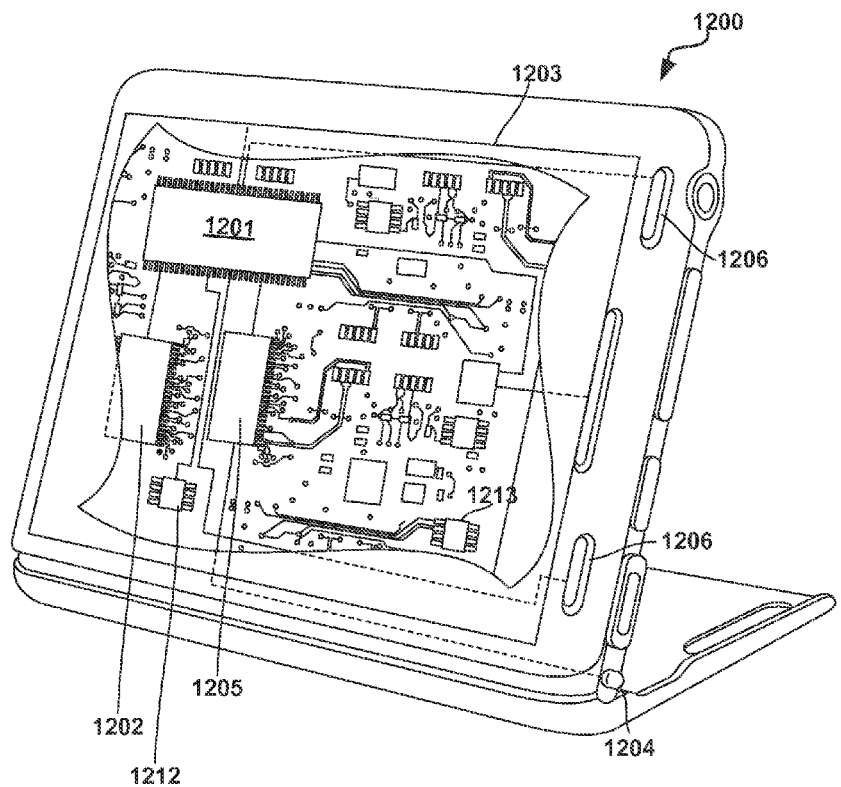
FIG. 12 is a component block diagram of a mobile computing device suitable for use with the various embodiments.

FIG. 12 is a system block diagram of a mobile device suitable for use with any of the embodiments. A typical mobile device 1200 may include a processor 1201 coupled to internal memory 1202, a display 1203, and to a speaker 1204. Additionally, the mobile device may include an antenna 1204 for sending and receiving electromagnetic radiation that may be connected to a wireless data link and/or cellular telephone transceiver 1205 coupled to the processor 1201 and a mobile multimedia broadcast receiver 1206 coupled to the processor. Mobile devices 1200 typically also include menu selection buttons or rocker switches for receiving user inputs.

Figure 13:
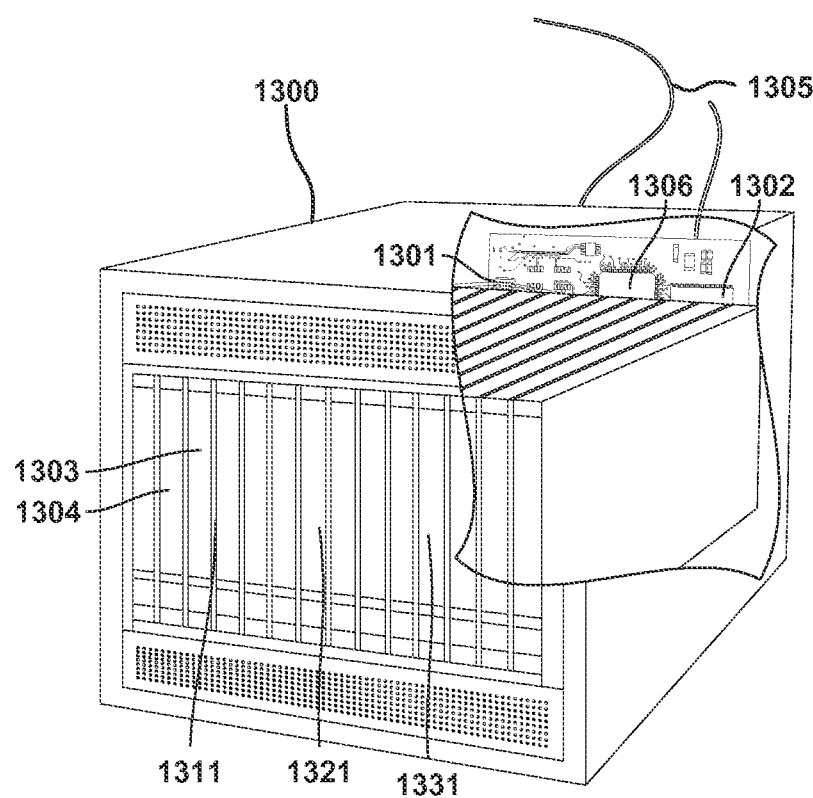
FIG. 13 is a component block diagram of a server computing device suitable for use with the various embodiments.

The various embodiments may be implemented on any of a variety of commercially available server devices, such as the server 1300 illustrated in FIG. 13. Such a server 1300 typically includes a processor 1301, and may include multiple processor systems 1311, 1321, 1331, one or more of which may be or include multi-core processors. The processor 1301 may be coupled to volatile memory 1302 and a large capacity nonvolatile memory, such as a disk drive 1303. The server 1300 may also include a floppy disc drive, compact disc (CD) or DVD disc drive coupled to the processor 1301. The server 1300 may also include network access ports 1304 coupled to the processor 1301 for establishing data connections with a network 1305, such as a local area network coupled to other broadcast system computers and servers.

Figure 14:
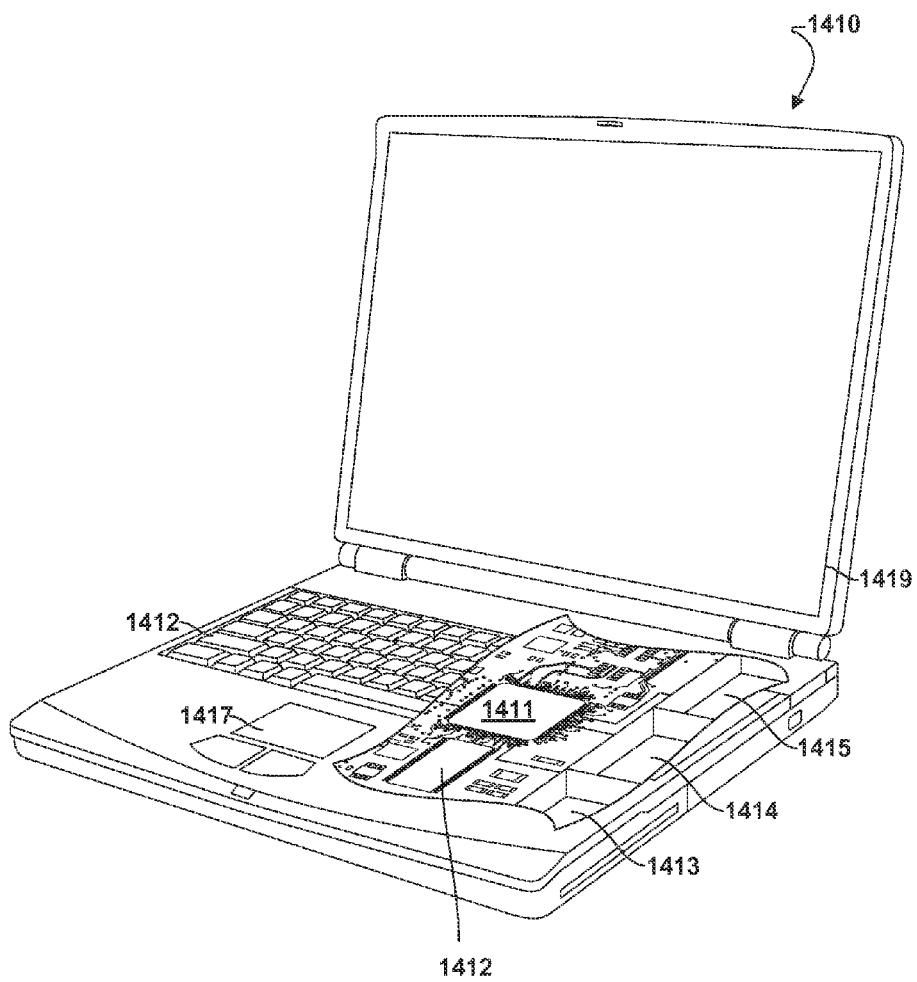
FIG. 14 is a component block diagram of a notebook computing device suitable for use with the various embodiments.

The embodiments described above may also be implemented within a variety of personal computing devices, such as a laptop computer 1410 as illustrated in FIG. 14. Many laptop computers include a touch pad touch surface 1417 that serves as the computer's pointing device, and thus may receive drag, scroll, and flick gestures similar to those implemented on mobile computing devices equipped with a touch screen display and described above. A laptop computer 1410 will typically include a processor 1411 coupled to volatile memory 1412 and a large capacity nonvolatile memory, such as a disk drive 1413 of Flash memory. The computer 1410 may also include a floppy disc drive 1414 and a compact disc (CD) drive 1415 coupled to the processor 1411. The computer device 1410 may also include a number of connector ports coupled to the processor 1411 for establishing data connections or receiving external memory devices, such as a USB or FireWire® connector sockets, or other network connection circuits for coupling the processor 1411 to a network. In a notebook configuration, the computer housing includes the touchpad 1417, the keyboard 1412, and the display 1419 all coupled to the processor 1411. Other configurations of computing device may include a computer mouse or trackball coupled to the processor (e.g., via a USB input) as are well known, which may also be use in conjunction with the various embodiments.

The processors 1201, 1301, 1311, 1321, 1331, and 1411 may be any programmable microprocessor, microcomputer or multiple processor chip or chips that can be configured by software instructions (applications) to perform a variety of functions, including the functions of the various embodiments described above. In some devices, multiple processors 1201, 1301, 1311, 1321, 1331, and 1411 may be provided, such as one processor dedicated to wireless communication functions and one processor dedicated to running other applications. Typically, software applications may be stored in the internal memory 1102, 1202, and 1203 before they are accessed and loaded into the processor 1201, 1301, 1311, 1321, 1331, and 1411. The processor 1201, 1301, 1311, 1321, 1331, and 1411 may include internal memory sufficient to store the application software instructions. In many devices the internal memory may be a volatile or nonvolatile memory, such as flash memory, or a mixture of both. For the purposes of this description, a general reference to memory refers to memory accessible by the processor 1201, 1301, 1311, 1321, 1331, and 1411 including internal memory or removable memory plugged into the device and memory within the processor 1201, 1301, 1311, 1321, 1331, and 1411 itself.

Since the methods of the various embodiments may be executed on a mobile device and other computer platforms, the methods may be implemented in an application or processor-executable instructions stored on a non-transitory computer readable medium that directs the mobile device or other computer device having a computer platform to perform the operations of the method. The computer readable medium may be the memory of the server, or may be in a database accessible by the mobile device. Further, the non-transitory computer readable medium may be in a secondary storage media that is loadable onto a wireless communications device computer platform, such as a magnetic disk or tape, optical disk, hard disk, flash memory, or other storage media as is known in the art.

The foregoing method descriptions and the process flow diagrams are provided merely as illustrative examples and are not intended to require or imply that the blocks of the various embodiments must be performed in the order presented. As will be appreciated by one of skill in the art the order of steps in the foregoing embodiments may be performed in any order. Words such as "thereafter," "then," "next," etc. are not intended to limit the order of the blocks; these words are simply used to guide the reader through the description of the methods. Further, any reference to claim elements in the singular, for example, using the articles "a," "an" or "the" is not to be construed as limiting the element to the singular.

In one or more exemplary embodiments, the functions described may be implemented in hardware, software, firmware, or any combination thereof. If implemented in software, the functions may be stored as one or more instructions or code on a non-transitory computer-readable medium. A non-transitory storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

While the invention has been particularly shown and described with reference to a preferred embodiment thereof, it will be understood by those skilled in the art that various changes in form and detail may be made without departing from the scope of the present invention as set forth in the following claims. Furthermore, although elements of the invention may be described or claimed in the singular, the plural is contemplated unless limitation to the singular is explicitly stated.

What is claimed is:

1. A method of altering a functionality of a wireless communication device, comprising:
   gathering data regarding a user of a first wireless communication device;
   creating a user profile based upon the gathered user data;
   transmitting the user profile to a second wireless communication device; and
   altering a device functionality setting of the second wireless communication device based upon the user profile.

2. The method of claim 1, wherein creating the user profile based upon the gathered user data comprises interpreting data obtained from a calendar application of the first wireless communication device.

3. The method of claim 2, wherein interpreting data obtained from the calendar application of the first wireless communication device comprises interpreting a user schedule.

4. The method of claim 1, wherein creating the user profile based upon the gathered user data comprises interpreting types of software applications used by a user of the first wireless communication device.

5. The method of claim 1, wherein creating the user profile based upon the gathered user data comprises interpreting contents of communications on the first wireless communication device.

6. The method of claim 5, wherein interpreting contents of communications on the first wireless communication device comprises interpreting content in an email message sent by a user of the first wireless communication device.

7. The method of claim 1, wherein creating the user profile based upon the gathered user data comprises interpreting data obtained from a social media application of the first wireless communication device.

8. The method of claim 1, wherein creating the user profile based upon the gathered user data comprises interpreting financial information relating to a user obtained from the first wireless communication device.

9. The method of claim 1, wherein creating the user profile based upon the gathered user data comprises interpreting data obtained from a web browser of the first wireless communication device.

10. The method of claim 9, wherein interpreting data obtained from the web browser of the first wireless communication device comprises interpreting a history of Internet searches performed by the user using the web browser.

11. The method of claim 9, wherein interpreting data obtained from the web browser of the first wireless communication device comprises interpreting types of websites accessed by the user using the web browser.

12. The method of claim 9, wherein interpreting data obtained from the web browser of the first wireless communication device comprises interpreting content loaded from websites accessed by the user using the web browser.

13. The method of claim 1, wherein creating the user profile based upon the gathered user data comprises interpreting location information obtained from the first wireless communication device.

14. The method of claim 13, wherein interpreting location information obtained from the first wireless communication device comprises interpreting information regarding movements of the first wireless communication device.

15. The method of claim 1, wherein creating the user profile based upon the gathered user data comprises interpreting data obtained from a global positioning system receiver of first wireless communication device.

16. The method of claim 1, wherein creating the user profile based upon the gathered user data comprises interpreting data obtained from a media player operating on the first wireless communication device.

17. The method of claim 1, wherein creating the user profile based upon the gathered user data comprises interpreting data obtained from a personal monitoring device.

18. The method of claim 17, wherein interpreting data obtained from the personal monitoring device comprises interpreting data obtained from a heart rate monitor.

19. The method of claim 17, wherein interpreting data obtained from the personal monitoring device comprises interpreting data obtained from a blood glucose meter.

20. The method of claim 17, wherein interpreting data obtained from the personal monitoring device comprises interpreting data obtained from a breathalyzer.

21. The method of claim 1, wherein creating the user profile based upon the gathered user data comprises interpreting information regarding the user received from an external device in communication with the first wireless communication device.

22. The method of claim 21, wherein interpreting information regarding the user received from the external device in communication with the first wireless communication device comprises interpreting information received from an external user monitoring device selected from the group of a medical monitoring device, and an exercise device.

23. The method of claim 1, wherein creating the user profile based upon the gathered user data comprises interpreting information collected regarding the user of the first wireless communication device from an external database.

24. The method of claim 1, wherein:
   the first wireless communication device comprises a video camera; and
   creating the user profile based upon the gathered user data comprises interpreting contents of a video recorded by the video camera of the first wireless communication device.

25. The method of claim 1, wherein creating the user profile comprises performing a psychological evaluation based upon the gathered user data.

26. The method of claim 1, wherein creating the user profile comprises making a medical diagnosis based upon the gathered user data.

27. The method of claim 1, wherein the second wireless communication device includes a graphic user interface (GUI) and altering the device functionality setting of the second wireless communication device comprises altering the GUI of the second wireless communication device.

28. A communication system, comprising:
- means for gathering data regarding a user of a first wireless communication device;
- means for creating a user profile based upon the gathered user data;
- means for transmitting the user profile to a second wireless communication device; and
- means for altering a device functionality setting of the second wireless communication device based upon the user profile.

29. The communication system of claim 28, wherein means for creating the user profile based upon the gathered user data comprises means for interpreting data obtained from a calendar application of the first wireless communication device.

30. The communication system of claim 29, wherein means for interpreting data obtained from the calendar application of the first wireless communication device comprises means for interpreting a user schedule.

31. The communication system of claim 28, wherein means for creating the user profile based upon the gathered user data comprises means for interpreting types of software applications used by a user of the first wireless communication device.

32. The communication system of claim 28, wherein means for creating the user profile based upon the gathered user data comprises means for interpreting contents of communications on the first wireless communication device.

33. The communication system of claim 32, wherein means for interpreting contents of communications on the first wireless communication device comprises means for interpreting content in an email message sent by a user of the first wireless communication device.

34. The communication system of claim 28, wherein means for creating the user profile based upon the gathered user data comprises means for interpreting data obtained from a social media application of the first wireless communication device.

35. The communication system of claim 28, wherein means for creating the user profile based upon the gathered user data comprises means for interpreting financial information relating to a user obtained from the first wireless communication device.

36. The communication system of claim 28, wherein means for creating the user profile based upon the gathered user data comprises means for interpreting data obtained from a web browser of the first wireless communication device.

37. The communication system of claim 36, wherein means for interpreting data obtained from the web browser of the first wireless communication device comprises means for interpreting a history of internet searches performed by the user using the web browser.

38. The communication system of claim 36, wherein means for interpreting data obtained from the web browser of the first wireless communication device comprises means for interpreting types of websites accessed by the user using the web browser.

39. The communication system of claim 36, wherein means for interpreting data obtained from the web browser of the first wireless communication device comprises means for interpreting content loaded from websites accessed by the user using the web browser.

40. The communication system of claim 28, wherein means for creating the user profile based upon the gathered user data comprises means for interpreting location information obtained from the first wireless communication device.

41. The communication system of claim 40, wherein means for interpreting location information obtained from the first wireless communication device comprises means for interpreting information regarding movements of the first wireless communication device.

42. The communication system of claim 28, wherein means for creating the user profile based upon the gathered user data comprises means for interpreting data obtained from a global positioning system receiver of first wireless communication device.

43. The communication system of claim 28, wherein means for creating the user profile based upon the gathered user data comprises means for interpreting data obtained from a media player operating on the first wireless communication device.

44. The communication system of claim 28, wherein means for creating the user profile based upon the gathered user data comprises means for interpreting data obtained from a personal monitoring device.

45. The communication system of claim 44, wherein means for interpreting data obtained from the personal monitoring device comprises means for interpreting data obtained from a heart rate monitor.

46. The communication system of claim 44, wherein means for interpreting data obtained from the personal monitoring device comprises means for interpreting data obtained from a blood glucose meter.

47. The communication system of claim 44, wherein means for interpreting data obtained from the personal monitoring device comprises means for interpreting data obtained from a breathalyzer.

48. The communication system of claim 28, wherein means for creating the user profile based upon the gathered user data comprises means for interpreting information regarding the user received from an external device in communication with the first wireless communication device.

49. The communication system of claim 48, wherein means for interpreting information regarding the user received from the external device in communication with the first wireless communication device comprises means for interpreting information received from an external user monitoring device selected from the group of a medical monitoring device and an exercise device.

50. The communication system of claim 28, wherein means for creating the user profile based upon the gathered user data comprises means for interpreting information collected regarding the user of the first wireless communication device from an external database.

51. The communication system of claim 28, wherein means for creating the user profile based upon the gathered user data comprises means for interpreting contents of a video recorded by a video camera of the first wireless communication device.

52. The communication system of claim 28, wherein means for creating the user profile comprises means for performing a psychological evaluation based upon the gathered user data.

53. The communication system of claim 28, wherein means for creating the user profile comprises means for making a medical diagnosis based upon the gathered user data.

54. The communication system of claim 28, wherein means for altering the device functionality setting of the second wireless communication device comprises means for altering a graphical user interface (GUI) of the second wireless communication device.

55. A communication system, comprising:
a first wireless communication device comprising a wireless transmitter, a memory, and a processor coupled to the wireless transmitter and the memory of the first wireless communication device; and
a second wireless communication device comprising a receiver configured to receive signals transmitted by the wireless transmitter, a second memory, and a processor coupled to the receiver and second memory of the second wireless communication device,
wherein the first wireless communication device processor is configured with processor-executable instructions to perform operations comprising:
gathering data regarding a user;
creating a user profile based upon the gathered user data; and
transmitting the user profile to the second wireless communication device, and
wherein the second wireless communication device processor is configured with processor-executable instructions to perform operations comprising:
receiving the user profile transmitted by the first wireless communication device; and
altering a device functionality setting of the second wireless communication device based upon the user profile.

56. The communication system of claim 55, wherein the first wireless communication device processor is configured with processor-executable instructions to perform operations such that creating the user profile based upon the gathered user data comprises interpreting data obtained from a calendar application of the first wireless communication device.

57. The communication system of claim 56, wherein the first wireless communication device processor is configured with processor-executable instructions to perform operations such that interpreting data obtained from the calendar application of the first wireless communication device comprises interpreting a user schedule.

58. The communication system of claim 55, wherein the first wireless communication device processor is configured with processor-executable instructions to perform operations such that creating the user profile based upon the gathered user data comprises interpreting types of software applications used by a user of the first wireless communication device.

59. The communication system of claim 55, wherein the first wireless communication device processor is configured with processor-executable instructions to perform operations such that creating the user profile based upon the gathered user data comprises interpreting contents of communications on the first wireless communication device.

60. The communication system of claim 59, wherein the first wireless communication device processor is configured with processor-executable instructions to perform operations such that interpreting contents of communications on the first wireless communication device comprises interpreting content in an email message sent by a user of the first wireless communication device.

61. The communication system of claim 55, wherein the first wireless communication device processor is configured with processor-executable instructions to perform operations such that creating the user profile based upon the gathered user data comprises interpreting data obtained from a social media application of the first wireless communication device.

62. The communication system of claim 55, wherein the first wireless communication device processor is configured with processor-executable instructions to perform operations such that creating the user profile based upon the gathered user data comprises interpreting financial information relating to a user obtained from the first wireless communication device.

63. The communication system of claim 55, wherein the first wireless communication device processor is configured with processor-executable instructions to perform operations such that creating the user profile based upon the gathered user data comprises interpreting data obtained from a web browser of the first wireless communication device.

64. The communication system of claim 63, wherein the first wireless communication device processor is configured with processor-executable instructions to perform operations such that interpreting data obtained from the web browser of the first wireless communication device comprises interpreting a history of Internet searches performed by the user using the web browser.

65. The communication system of claim 63, wherein the first wireless communication device processor is configured with processor-executable instructions to perform operations such that interpreting data obtained from the web browser of the first wireless communication device comprises interpreting types of websites accessed by the user using the web browser.

66. The communication system of claim 63, wherein the first wireless communication device processor is configured with processor-executable instructions to perform operations such that interpreting data obtained from the web browser of the first wireless communication device comprises interpreting content loaded from websites accessed by the user using the web browser.

67. The communication system of claim 55, wherein the first wireless communication device processor is configured with processor-executable instructions to perform operations such that creating the user profile based upon the gathered user data comprises interpreting location information obtained from the first wireless communication device.

68. The communication system of claim 67, wherein the first wireless communication device processor is configured with processor-executable instructions to perform operations such that interpreting location information obtained from the first wireless communication device comprises interpreting information regarding movements of the first wireless communication device.

69. The communication system of claim 55, wherein the first wireless communication device processor is configured with processor-executable instructions to perform operations such that creating the user profile based upon the gathered user data comprises interpreting data obtained from a global positioning system receiver of first wireless communication device.

70. The communication system of claim 55, wherein the first wireless communication device processor is configured with processor-executable instructions to perform operations such that creating the user profile based upon the gathered user data comprises interpreting data obtained from a media player operating on the first wireless communication device.

71. The communication system of claim 55, wherein the first wireless communication device processor is configured with processor-executable instructions to perform operations such that creating the user profile based upon the gathered user data comprises interpreting data obtained from a personal monitoring device.

72. The communication system of claim 71, wherein the first wireless communication device processor is configured with processor-executable instructions to perform operations such that interpreting data obtained from the personal monitoring device comprises interpreting data obtained from a heart rate monitor.

73. The communication system of claim 71, wherein the first wireless communication device processor is configured with processor-executable instructions to perform operations such that interpreting data obtained from the personal monitoring device comprises interpreting data obtained from a blood glucose meter.

74. The communication system of claim 71, wherein the first wireless communication device processor is configured with processor-executable instructions to perform operations such that interpreting data obtained from the personal monitoring device comprises interpreting data obtained from a breathalyzer.

75. The communication system of claim 55, wherein the first wireless communication device processor is configured with processor-executable instructions to perform operations such that creating the user profile based upon the gathered user data comprises interpreting information regarding the user received from an external device in communication with the first wireless communication device.

76. The communication system of claim 75, wherein the first wireless communication device processor is configured with processor-executable instructions to perform operations such that interpreting information regarding the user received from the external device in communication with the first wireless communication device comprises interpreting information received from an external user monitoring device selected from the group of a medical monitoring device, and an exercise device.

77. The communication system of claim 55, wherein the first wireless communication device processor is configured with processor-executable instructions to perform operations such that creating the user profile based upon the gathered user data comprises interpreting information collected regarding the user of the first wireless communication device from an external database.

78. The communication system of claim 55, wherein:
the first wireless communication device further comprises a video camera; and
the first wireless communication device processor is configured with processor-executable instructions to perform operations such that creating the user profile based upon the gathered user data comprises interpreting contents of a video recorded by the video camera of the first wireless communication device.

79. The communication system of claim 55, wherein the first wireless communication device processor is configured with processor-executable instructions to perform operations such that creating the user profile comprises performing a psychological evaluation based upon the gathered user data.

80. The communication system of claim 55, wherein the first wireless communication device processor is configured with processor-executable instructions to perform operations such that creating the user profile comprises making a medical diagnosis based upon the gathered user data.

81. The communication system of claim 55, wherein:
the second wireless communication device includes a graphic user interface (GUI); and
the second wireless communication device processor is configured with processor-executable instructions to perform operations such that altering the device functionality setting of the second wireless communication device comprises altering the GUI of the second wireless communication device.

82. A communication device, comprising:
a transceiver;
a memory; and
a processor coupled to the memory and the transceiver, wherein the processor is configured with processor-executable instructions to perform operations comprising:
receiving user data regarding a user of a second communication device;
creating a user profile based upon the received user data; and
altering a device functionality setting of the communication device based upon the user profile.

83. The communication device of claim 82, wherein the processor is configured with processor-executable instructions such that creating the user profile based upon the received user data comprises interpreting data obtained from a calendar application of the second communication device.

84. The communication device of claim 83, wherein the processor is configured with processor-executable instructions such that interpreting data obtained from the calendar application of the second communication device comprises interpreting a user schedule.

85. The communication device of claim 82, wherein the processor is configured with processor-executable instructions such that creating the user profile based upon the received user data comprises interpreting types of software applications used by a user of the second communication device.

86. The communication device of claim 82, wherein the processor is configured with processor-executable instructions such that creating the user profile based upon the received user data comprises interpreting contents of communications on the second communication device.

87. The communication device of claim 86, wherein the processor is configured with processor-executable instructions such that interpreting contents of communications on the second communication device comprises interpreting content in an email message sent by a user of the second communication device.

88. The communication device of claim 82, wherein the processor is configured with processor-executable instructions such that creating the user profile based upon the received user data comprises interpreting data obtained from a social media application of the second communication device.

89. The communication device of claim 82, wherein the processor is configured with processor-executable instructions such that creating the user profile based upon the received user data comprises interpreting financial information relating to a user obtained from the second communication device.

90. The communication device of claim 82, wherein the processor is configured with processor-executable instructions such that creating the user profile based upon the received user data comprises interpreting data obtained from a web browser of the second communication device.

91. The communication device of claim 90, wherein the processor is configured with processor-executable instructions such that interpreting data obtained from the web browser of the second communication device comprises interpreting a history of Internet searches performed by the user using the web browser.

92. The communication device of claim 90, wherein the processor is configured with processor-executable instructions such that interpreting data obtained from the web browser of the second communication device comprises interpreting types of websites accessed by the user using the web browser.

93. The communication device of claim 90, wherein the processor is configured with processor-executable instructions such that interpreting data obtained from the web browser of the second communication device comprises interpreting content loaded from websites accessed by the user using the web browser.

94. The communication device of claim 82, wherein the processor is configured with processor-executable instructions such that creating the user profile based upon the received user data comprises interpreting location information obtained from the second communication device.

95. The communication device of claim 94, wherein the processor is configured with processor-executable instructions such that interpreting location information obtained from the second communication device comprises interpreting information regarding movements of the second communication device.

96. The communication device of claim 82, wherein the processor is configured with processor-executable instructions such that creating the user profile based upon the received user data comprises interpreting data obtained from a global positioning system receiver of second communication device.

97. The communication device of claim 82, wherein the processor is configured with processor-executable instructions such that creating the user profile based upon the received user data comprises interpreting data obtained from a media player operating on the second communication device.

98. The communication device of claim 82, wherein the processor is configured with processor-executable instructions such that creating the user profile based upon the received user data comprises interpreting data obtained from a personal monitoring device.

99. The communication device of claim 98, wherein the processor is configured with processor-executable instructions such that interpreting data obtained from the personal monitoring device comprises interpreting data obtained from a heart rate monitor.

100. The communication device of claim 98, wherein the processor is configured with processor-executable instructions such that interpreting data obtained from the personal monitoring device comprises interpreting data obtained from a blood glucose meter.

101. The communication device of claim 98, wherein the processor is configured with processor-executable instructions such that interpreting data obtained from the personal monitoring device comprises interpreting data obtained from a breathalyzer.

102. The communication device of claim 82, wherein the processor is configured with processor-executable instructions such that creating the user profile based upon the received user data comprises interpreting information regarding the user received from an external device in communication with the second communication device.

103. The communication device of claim 102, wherein the processor is configured with processor-executable instructions such that interpreting information regarding the user received from the external device in communication with the second communication device comprises interpreting information received from an external user monitoring device selected from the group of a medical monitoring device and an exercise device.

104. The communication device of claim 82, wherein the processor is configured with processor-executable instructions such that creating the user profile based upon the received user data comprises interpreting information collected regarding the user of the second communication device from an external database.

105. The communication device of claim 82, wherein the processor is configured with processor-executable instructions such that creating the user profile based upon the received user data comprises interpreting contents of a video recorded by a video camera of the second communication device.

106. The communication device of claim 82, wherein the processor is configured with processor-executable instructions such that creating the user profile comprises performing a psychological evaluation based upon the received user data.

107. The communication device of claim 82, wherein the processor is configured with processor-executable instructions such that creating a user profile comprises making a medical diagnosis based upon the received user data.

108. The communication device of claim 82, wherein the processor is configured with processor-executable instructions such that altering the device functionality setting of the communication device comprises altering a graphical user interface (GUI) of the communication device.

109. A non-transitory computer readable storage medium having stored thereon processor-executable software instructions configured to cause a processor of a communication device to perform operations comprising:
 receiving user data regarding a user of a second communication device;
 creating a user profile based upon the received user data; and
 altering a device functionality setting of the communication device based upon the user profile.

110. The non-transitory computer readable storage medium of claim 109, wherein the stored processor-executable software instructions are configured to cause a processor to perform operations such that creating the user profile based upon the received user data comprises interpreting data obtained from a calendar application of the second communication device.

111. The non-transitory computer readable storage medium of claim 110, wherein the stored processor-executable software instructions are configured to cause a processor to perform operations such that interpreting data obtained from the calendar application of the second communication device comprises interpreting a user schedule.

112. The non-transitory computer readable storage medium of claim 109, wherein the stored processor-executable software instructions are configured to cause a processor to perform operations such that creating the user profile based upon the received user data comprises interpreting types of software applications used by a user of the second communication device.

113. The non-transitory computer readable storage medium of claim 109, wherein the stored processor-executable software instructions are configured to cause a processor to perform operations such that creating the user profile based upon the received user data comprises interpreting contents of communications on the second communication device.

114. The non-transitory computer readable storage medium of claim 113, wherein the stored processor-executable software instructions are configured to cause a processor to perform operations such that interpreting contents of communications on the second communication device comprises interpreting content in an email message sent by a user of the second communication device.

115. The non-transitory computer readable storage medium of claim 109, wherein the stored processor-executable software instructions are configured to cause a processor to perform operations such that creating the user profile based upon the received user data comprises interpreting data obtained from a social media application of the second communication device.

116. The non-transitory computer readable storage medium of claim 109, wherein the stored processor-executable software instructions are configured to cause a processor to perform operations such that creating the user profile based upon the received user data comprises interpreting financial information relating to a user obtained from the second communication device.

117. The non-transitory computer readable storage medium of claim 109, wherein the stored processor-executable software instructions are configured to cause a processor to perform operations such that creating the user profile based upon the received user data comprises interpreting data obtained from a web browser of the second communication device.

118. The non-transitory computer readable storage medium of claim 117, wherein the stored processor-executable software instructions are configured to cause a processor to perform operations such that interpreting data obtained from the web browser of the second communication device comprises interpreting a history of internet searches performed by the user using the web browser.

119. The non-transitory computer readable storage medium of claim 117, wherein the stored processor-executable software instructions are configured to cause a processor to perform operations such that interpreting data obtained from the web browser of the second communication device comprises interpreting types of websites accessed by the user using the web browser.

120. The non-transitory computer readable storage medium of claim 117, wherein the stored processor-executable software instructions are configured to cause a processor to perform operations such that interpreting data obtained from the web browser of the second communication device comprises interpreting content loaded from websites accessed by the user using the web browser.

121. The non-transitory computer readable storage medium of claim 109, wherein the stored processor-executable software instructions are configured to cause a processor to perform operations such that creating the user profile based upon the received user data comprises interpreting location information obtained from the second communication device.

122. The non-transitory computer readable storage medium of claim 121, wherein the stored processor-executable software instructions are configured to cause a processor to perform operations such that interpreting location information obtained from the second communication device comprises interpreting information regarding movements of the second communication device.

123. The non-transitory computer readable storage medium of claim 109, wherein the stored processor-executable software instructions are configured to cause a processor to perform operations such that creating the user profile based upon the received user data comprises interpreting data obtained from a global positioning system receiver of second communication device.

124. The non-transitory computer readable storage medium of claim 109, wherein the stored processor-executable software instructions are configured to cause a processor to perform operations such that creating the user profile based upon the received user data comprises interpreting data obtained from a media player operating on the second communication device.

125. The non-transitory computer readable storage medium of claim 109, wherein the stored processor-executable software instructions are configured to cause a processor to perform operations such that creating the user profile based upon the received user data comprises interpreting data obtained from a personal monitoring device.

126. The non-transitory computer readable storage medium of claim 125, wherein the stored processor-executable software instructions are configured to cause a processor to perform operations such that interpreting data obtained from the personal monitoring device comprises interpreting data obtained from a heart rate monitor.

127. The non-transitory computer readable storage medium of claim 125, wherein the stored processor-executable software instructions are configured to cause a processor to perform operations such that interpreting data obtained from the personal monitoring device comprises interpreting data obtained from a blood glucose meter.

128. The non-transitory computer readable storage medium of claim 125, wherein the stored processor-executable software instructions are configured to cause a processor to perform operations such that interpreting data obtained from the personal monitoring device comprises interpreting data obtained from a breathalyzer.

129. The non-transitory computer readable storage medium of claim 109, wherein the stored processor-executable software instructions are configured to cause a processor to perform operations such that creating the user profile based upon the received user data comprises interpreting information regarding the user received from an external device in communication with the second communication device.

130. The non-transitory computer readable storage medium of claim 129, wherein the stored processor-executable software instructions are configured to cause a processor to perform operations such that interpreting information regarding the user received from the external device in communication with the second communication device comprises interpreting information received from an external user monitoring device selected from the group of a medical monitoring device and an exercise device.

131. The non-transitory computer readable storage medium of claim 109, wherein the stored processor-executable software instructions are configured to cause a processor to perform operations such that creating the user profile based upon the received user data comprises interpreting information collected regarding the user of the second communication device from an external database.

132. The non-transitory computer readable storage medium of claim 109, wherein the stored processor-executable software instructions are configured to cause a processor to perform operations such that creating the user profile based upon the received user data comprises interpreting contents of a video recorded by a video camera of the second communication device.

133. The non-transitory computer readable storage medium of claim 109, wherein the stored processor-executable software instructions are configured to cause a processor to perform operations such that creating the user profile comprises performing a psychological evaluation based upon the received user data.

134. The non-transitory computer readable storage medium of claim 109, wherein the stored processor-executable software instructions are configured to cause a processor to perform operations such that creating the user profile comprises making a medical diagnosis based upon the received user data.

135. The non-transitory computer readable storage medium of claim 109, wherein the stored processor-executable software instructions are configured to cause a processor to perform operations such that altering the device functionality setting of the communication device comprises altering a graphical user interface (GUI) of the communication device.

* * * * *